(12) United States Patent
Miazga et al.

(10) Patent No.: US 7,308,318 B2
(45) Date of Patent: Dec. 11, 2007

(54) PERCUTANEOUS APPARATUS WITH ELECTRICAL COUPLING

(75) Inventors: Jay Miazga, Seattle, WA (US); Paul C. Leonard, Woodinville, WA (US); Chris Genau, Seattle, WA (US)

(73) Assignee: Meagan Medical, Inc., Vancouver, WA (US)

( * ) Notice: Subject to any disclaimer, the term of this patent is extended or adjusted under 35 U.S.C. 154(b) by 394 days.

(21) Appl. No.: 10/735,807

(22) Filed: Dec. 16, 2003

(65) Prior Publication Data

US 2004/0147995 A1 Jul. 29, 2004

Related U.S. Application Data

(60) Provisional application No. 60/433,800, filed on Dec. 16, 2002, provisional application No. 60/433,831, filed on Dec. 16, 2002, provisional application No. 60/433,861, filed on Dec. 16, 2002.

(51) Int. Cl.
*A61N 1/05* (2006.01)
(52) U.S. Cl. ...................................... 607/116; 128/907
(58) Field of Classification Search .................... 607/1, 607/2, 46, 48, 50, 115, 152, 148, 116, 149; 600/382, 386, 390, 393, 394
See application file for complete search history.

(56) References Cited

U.S. PATENT DOCUMENTS 6,208,893 B1 * 3/2001 Hofmann .................... 607/148

2001/0021869 A1 9/2001 Bishay et al.

OTHER PUBLICATIONS

U.S. Appl. No. 10/735,809, filed Dec. 16, 2003, Jay Miazga et al.
U.S. Appl. No. 10/735,808, filed Dec. 16, 2003, May Miazga et al.
Ghoname et al., "Percutaneous Electrical Nerve Stimulation for Low Back Pain," JAMA 281:818-23 (1999).
Ghoname et al., "The Effect of Stimulus Frequency on the Analgesic Response to Percutaneous Electrical Nerve Stimulation in Patients with Chronic Low Back Pain," Anesth. Analg. 88:841-6 (1999).
Ahmed et al., "Percutaneous Electrical Nerve Stimulation (PENS): A Complementary Therapy for the Management of Pain Secondary to Bony Metastasis," Clinical Journal of Pain 14:320-3 (1998).
Ahmed et al., "Percutaneous Electrical Nerve Stimulation: An Alternative to Antiviral Drugs for Herpes Zoster," Anesth. Analg. 87:911-4 (1998).

* cited by examiner

*Primary Examiner*—George R. Evanisko
(74) *Attorney, Agent, or Firm*—Blank Rome LLP

(57) ABSTRACT

Methods and apparatuses for electrically coupling to percutaneous probes wherein entry angles of the percutaneous probes are controllable. An apparatus in accordance with one embodiment of the invention includes a percutaneous electrode having a first segment with a first sharp end and a second segment with a second end, at least part of the first segment being aligned along an axis and at least part of the second segment being offset from the axis. The apparatus can further include a coupling member having an aperture with a wall portion, at least a portion of which is electrically conductive. The apparatuses include shaped support surfaces, and associated methods wherein a non-planar support surface can more easily match a recipient's skin surface contour for improved comfort and security upon attachment.

14 Claims, 27 Drawing Sheets

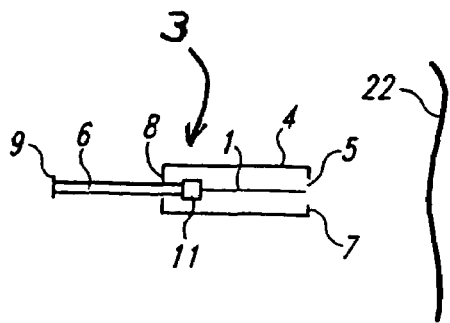
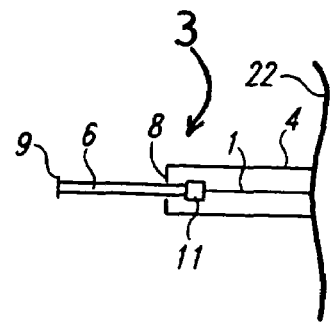
Fig. 1A    Fig. 1B
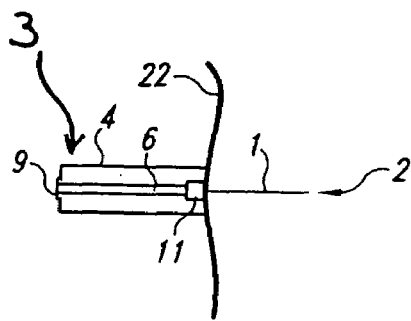
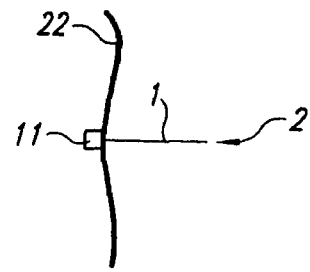
Fig. 1C    Fig. 1D
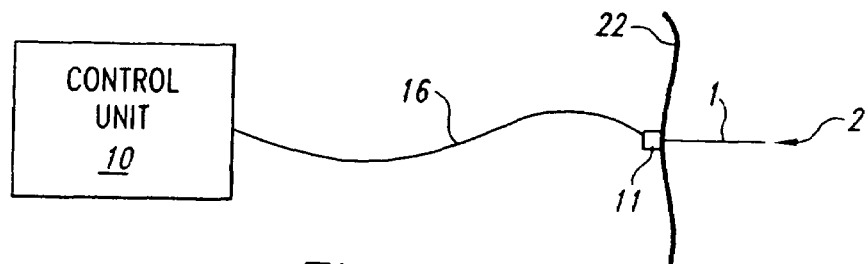
Fig. 1E
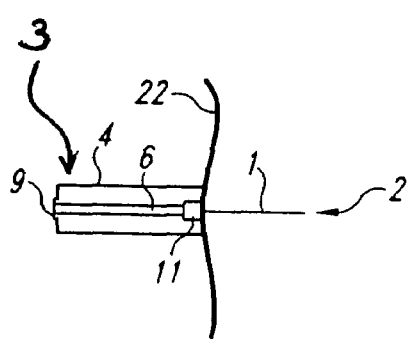
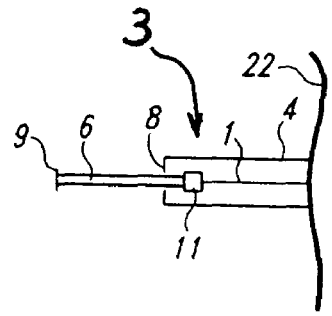
Fig. 1F    Fig. 1G

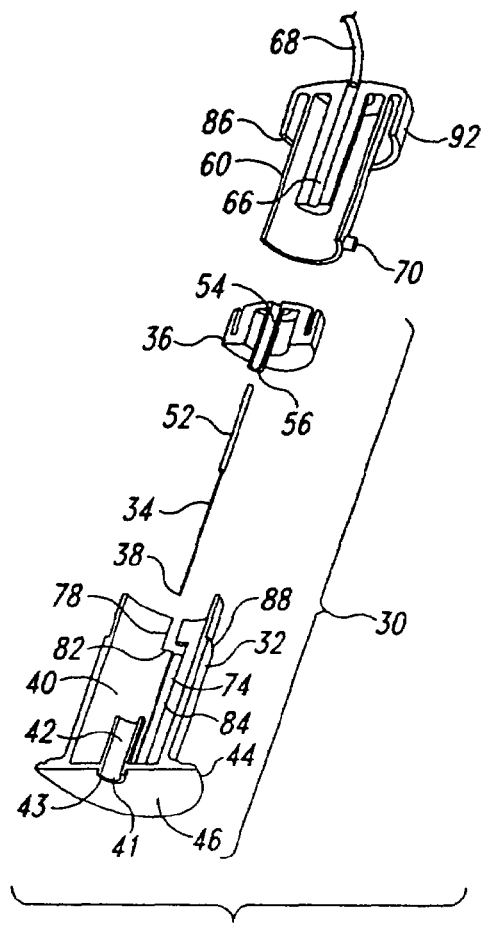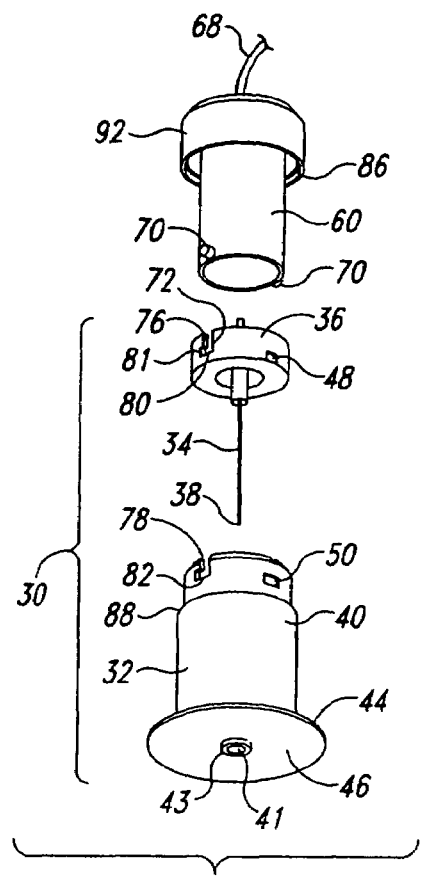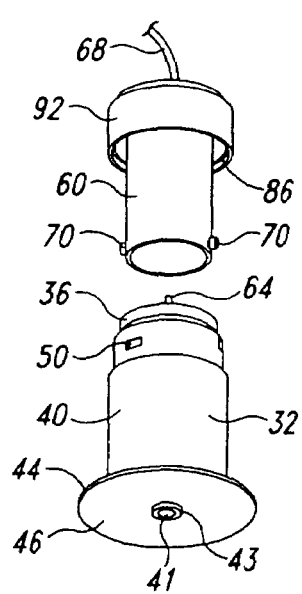

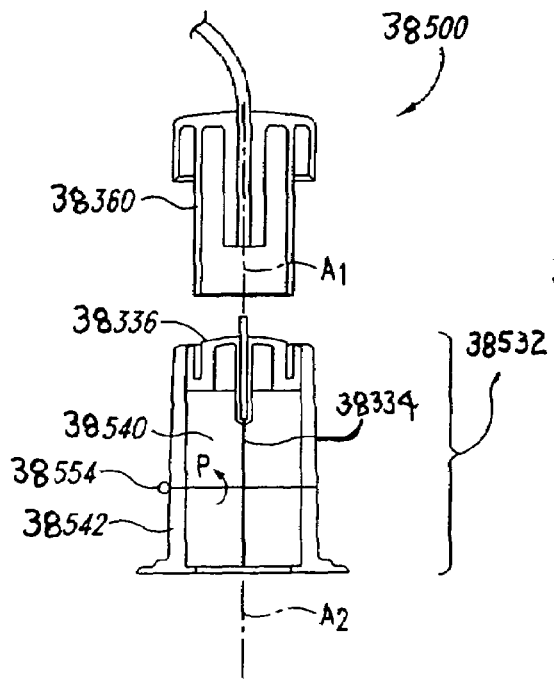
*Fig.* 38 A
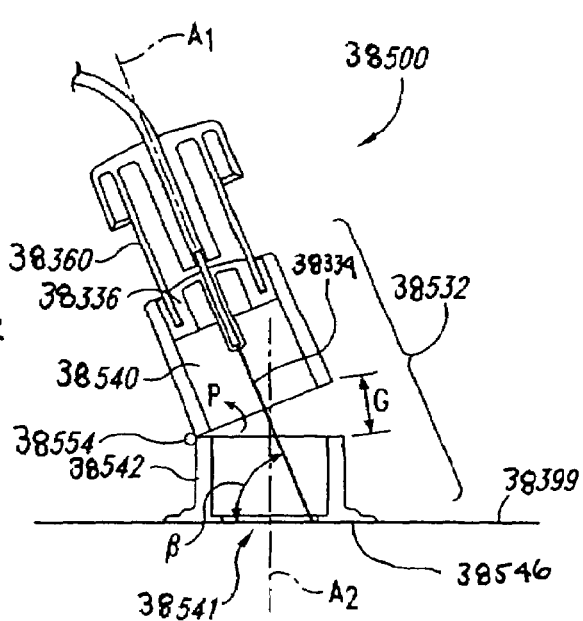
*Fig.* 38 B
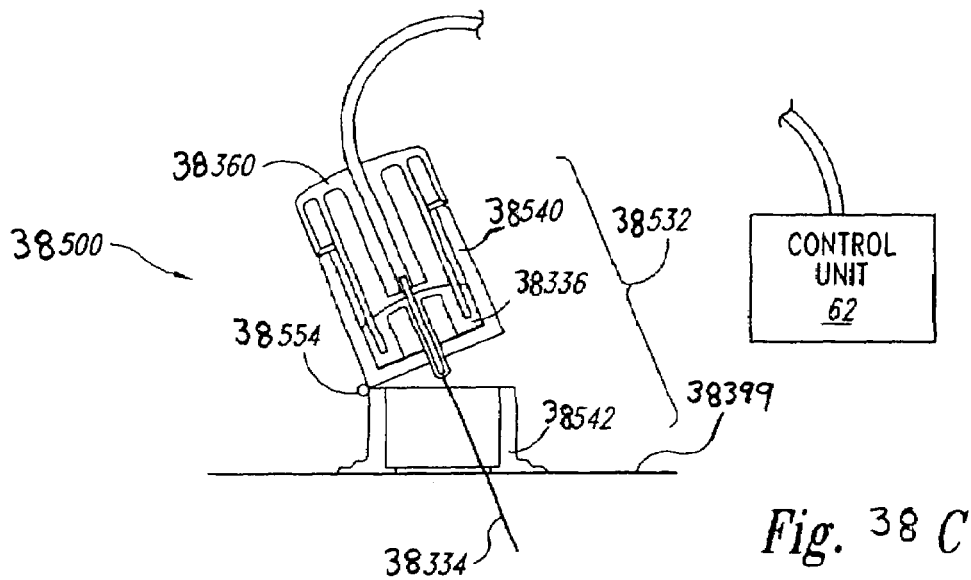
*Fig.* 38 C

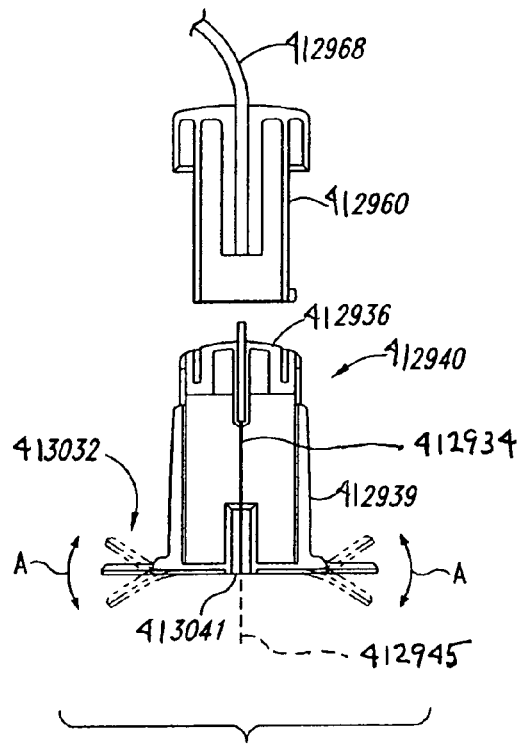
Fig. 41
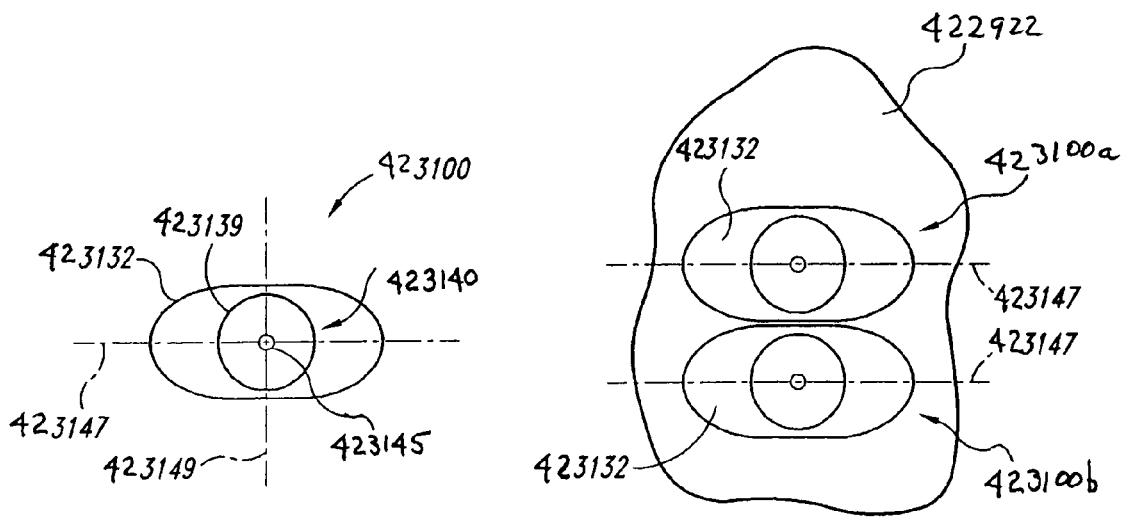
Fig. 42 A
Fig. 42 B

PERCUTANEOUS APPARATUS WITH ELECTRICAL COUPLING

REFERENCE TO RELATED APPLICATIONS

This application claims priority to the U.S. Provisional Applications Ser. Nos. 60/433,800, filed Dec. 16, 2002, 60/433,831, filed Dec. 16, 2002, and 60/433,861, filed Dec. 16, 2002, which are entirely incorporated herein by reference.

BACKGROUND

Electrical therapy has long been used in medicine to treat pain and other conditions. For example, transcutaneous electrical nerve stimulation (TENS) systems deliver electrical energy through electrode patches placed on the surface of a patient's skin to treat pain in tissue beneath and around the location of the patches. The efficacy of TENS systems in alleviating pain is questionable at best, however.

More recently, a technique in which electrodes are placed through the patient's skin into the target tissue has been proposed. Percutaneous Neuromodulation Therapy ("PNT") (also sometimes called Percutaneous Electrical Nerve Stimulation or "PENS") using percutaneously placed electrodes achieves significantly better pain relief results than TENS treatments using skin surface electrodes. That therapy is described in Ghoname et al., "Percutaneous Electrical Nerve Stimulation for Low Back Pain," JAMA 281:818-23 (1999); Ghoname et al., "The Effect of Stimulus Frequency on the Analgesic Response to Percutaneous Electrical Nerve Stimulation in Patients with Chronic Low Back Pain," Anesth. Analg. 88:841-6 (1999); Ahmed et al., "Percutaneous Electrical Nerve Stimulation (PENS): A Complementary Therapy for the Management of Pain Secondary to Bony Metastasis," Clinical Journal of Pain 14:320-3 (1998); and Ahmed et al., "Percutaneous Electrical Nerve Stimulation: An Alternative to Antiviral Drugs for Herpes Zoster," Anesth. Analg. 87:911-4 (1998). The contents of those references are incorporated herein by reference.

Thus far, PNT practitioners have used percutaneously placed acupuncture needles attached to waveform generators via cables and alligator clips to deliver the therapy to the patient. The foregoing arrangement and design of electrodes and generator are far from optimal. One drawback with some existing PNT techniques is that it can be difficult for practitioners to control the entry angle of the percutaneous electrode during insertion into the patient. As a result, the practitioner may not position the electrode at the most comfortable, convenient, or effective orientation, and accordingly may not deliver treatment in an optimal fashion. Another drawback with some existing PNT techniques is that the electrode can be difficult to manipulate and/or work around, particularly when multiple electrodes are used simultaneously on a relatively small portion of the patient's body. For example, the prior art has not addressed the issue of sharps protection for the patients' caregivers and other bystanders. Another drawback with the foregoing arrangement is that the alligator clips can be cumbersome to operate and can produce unreliable electrical connections. And yet another drawback is that it can be difficult to accurately position the needles in a manner that is secure and still comfortable for the recipient.

SUMMARY

The present invention is directed to methods and apparatuses for electrically coupling to percutaneous electrodes. An apparatus in accordance with one aspect of the invention includes an elongated percutaneous electrode having a first segment with a sharp first end and a second segment with a second end. At least part of the second segment can be configured to resiliently return to a neutral position, and can be spaced apart from at least part of the first segment by a separation distance when in the neutral position. The apparatus can further include a coupling member having an aperture with an electrically conductive portion. The aperture can be sized to removably receive at least part of the first segment and at least part of the second segment in contact with the electrically conductive portion.

In further aspects of the invention, the aperture can have a diameter smaller than the separation distance, and/or a generally circular cross-sectional shape, or a non-axisymmetric cross-sectional shape. In other embodiments, the at least part of the first segment can be aligned along an axis and the at least part of the second segment can be offset from the axis. In still further aspects of the invention, at least one of the first and second segments can be movable relative to the other so that the percutaneous electrode has a first configuration when the at least part of the first segment is spaced apart from the at least part of the second segment by a first distance, and a second configuration when the at least part of the first segment is spaced apart from the at least part of the second segment by a second distance less than the first distance, with a conductive material of the electrode being elastically changeable from the first configuration to the second configuration.

A method in accordance with another aspect of the invention includes moving at least one of a percutaneous electrode and an electrically conductive coupler relative to the other to receive a portion of the percutaneous electrode in an aperture of the conductive coupler. The method can further include contacting first and second segments of the percutaneous electrode with a conductive portion in the aperture while at least a part of a first segment of the percutaneous electrode faces toward at least a part of a second segment of the percutaneous electrode. The percutaneous electrode can then be deployed into a recipient's tissue.

In another aspect of the invention, contacting the first and second segments of the percutaneous electrode with the conductive portion can include forcing at least one of the first segment and the second segment towards the other. In another aspect of the invention, contacting the first and second segments of the percutaneous electrode with the conductive portion can include rotating at least one of the percutaneous electrode and the conductive coupler relative to the other while the percutaneous electrode is received in the aperture of the conductive coupler.

In one aspect of the invention, an apparatus includes a housing and a percutaneous probe movably disposed in the housing. The housing includes a first portion having a first axis and a second portion having a second axis. The first portion is coupled to the second portion and movable between a first position and a second position relative to the second portion. When the first portion is in the first position, the first axis is generally parallel to the second axis. When the first portion is in the second position, the first axis is generally transverse to the second axis.

In a further aspect of the invention, the first portion can be coupled to the second portion by a ball and socket connection, a hinge, or a flexible portion to permit relative movement between the first and second portions. In other aspects of the invention, the housing can further include a locking device to selectively restrict movement of the first portion relative to the second portion. In another aspect of the invention, the percutaneous probe can include an electrode, an acupuncture needle, a hollow needle, and/or a diagnostic probe.

In another aspect of the invention, an apparatus includes a percutaneous probe and a housing having a first portion and a second portion coupled to the first portion. The first portion is movable relative to the second portion to orient the percutaneous probe for insertion into the recipient's skin at a selected angle of less than 90 degrees relative to the recipient's skin. The percutaneous probe is movably disposed in the housing.

Other aspects of the invention are directed to methods for operating an apparatus for percutaneous application. One method includes positioning a housing at least proximate to a recipient's skin and moving a first portion of the housing relative to a second portion of the housing to orient a percutaneous probe at a selected angle of less than 90 degrees relative to the recipient's skin. The method further includes inserting a portion of the percutaneous probe into the recipient at the selected angle, withdrawing the percutaneous probe from the recipient, and stowing the percutaneous probe in the housing.

An apparatus in accordance with yet another aspect includes a housing having a probe portion disposed around a probe axis, the housing further having a non-planar support surface configured to face toward a recipient's skin, with the support surface having an exit aperture. A percutaneous probe having a sharp end can be movably positioned in the probe portion of the housing, with the percutaneous probe being movable along a probe axis relative to the housing between a stowed position with the sharp end located within the housing and a deployed position with the sharp end deployed through the exit aperture. The apparatus can further include an attachment device depending from the housing and configured to releasably attach the housing to the recipient's skin.

In further aspects of the invention, the support surface can have a shape that is asymmetric with respect to the probe axis. For example, the support surface can have an elliptical shape. In still another aspect of the invention, the support surface can be part of a flexible support member, with the flexible support member deflectable from a neutral position in two opposing directions toward the probe axis. In still a further aspect of the invention, the apparatus can include first and second percutaneous units, with each unit having a percutaneous probe in a housing, and with the size, shape, or size and shape of one of the housings being different than the corresponding size, shape, and/or size and shape of another of the housings.

The invention is also directed toward methods for operating a percutaneous apparatus. A method in accordance with one aspect of the invention includes placing a first percutaneous probe housing on a recipient's skin, with the first percutaneous probe housing carrying a first percutaneous probe and having a first support surface facing toward the recipient's skin generally transverse to the first percutaneous probe. The first surface can be non-axisymmetric relative to the first percutaneous probe and can have a first orientation relative to the recipient's spine. The first percutaneous probe can be deployed from the first housing into the recipient's skin, and the method can further include placing a second percutaneous probe housing on the recipient's skin, with the second percutaneous probe housing carrying a second percutaneous probe and having a second support surface facing toward the recipient's skin generally transverse to the second percutaneous probe. The second surface can be non-axisymmetric relative to the second probe and can have a second orientation relative to the recipient's spine different than the first orientation. The method can further include deploying the second percutaneous probe from the second housing into the recipient's skin.

A method in accordance with another aspect of the invention includes aligning a housing with a recipient's skin surface, with the housing carrying a percutaneous probe aligned along a probe axis. A flexible support member of the housing can be positioned at least proximate to the skin surface, with the flexible support member having a flexible support surface facing toward the skin surface and being deflectable from a neutral position in two opposing directions toward the probe axis. The method can further include bending the flexible support surface to at least approximately match a contour of the skin surface, releasably attaching the housing to the skin surface, and deploying the percutaneous probe from the housing into the skin surface.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the presenting invention. Moreover, in the drawings, like reference numerals designate corresponding parts through the several views.

FIGS. 1A-G are schematic illustrations of a percutaneous electrical therapy system according to one embodiment of the invention.

FIG. 1A shows electrode and sharp point protection assemblies wherein the electrode is in an undeployed and uninserted state.

FIG. 1B shows the electrode and sharp point protection assemblies of FIG. 1A during deployment but prior to insertion of the electrode into a patient's tissue.

FIG. 1C shows the electrode and sharp point protection assemblies of FIG. 1A during deployment and insertion of the electrode into the patient's tissue.

FIG. 1D shows the electrode of FIG. 1A inserted into the patient's tissue.

FIG. 1E shows the electrode of FIG. 1A attached to a control unit to provide percutaneous electrical therapy.

FIG. 1F shows the electrode and sharp point protection assemblies of FIG. 1A during undeployment but prior to removing the sharp point of the electrode from the patient's tissue.

FIG. 1G shows the electrode and sharp point protection assemblies of FIG. 1A during undeployment and after removing the sharp point of the electrode from the patient's tissue.

FIG. 2A shows a percutaneous electrical therapy system with electrode and sharp point protection assemblies wherein the electrode is in an undeployed and uninserted state.

FIG. 2B shows the percutaneous electrical therapy system of FIG. 2A during deployment, but prior to insertion, of the electrode.

FIG. 2C shows the percutaneous electrical therapy system of FIG. 2A with the electrode in a deployed and inserted state.

FIG. 2D shows the percutaneous electrical therapy system of FIG. 2A during undeployment of the electrode.

FIG. 2E shows the percutaneous electrical therapy system of FIG. 2A after the electrode has been undeployed.

FIG. 4 is an exploded sectional view of an electrode and sharp point protection assembly according to yet another embodiment of this invention.

FIG. 5 is a partially exploded elevational view of the embodiment of FIG. 4.

FIG. 6 is an elevational view of the embodiment of FIG. 4 showing the electrode and sharp point protection assemblies and an actuator tool.

FIG. 38A is a partially schematic, cross-sectional illustration of an apparatus configured to deploy a percutaneous probe in accordance with another embodiment of the invention.

FIG. 38B is a partially schematic, cross-sectional illustration of the apparatus of FIG. 38A positioned against the recipient's skin with the percutaneous probe oriented at a selected angle with respect to the skin.

FIG. 38C is a partially schematic, cross-sectional illustration of the apparatus of FIG. 38B with the percutaneous probe inserted into the recipient.

FIG. 41 is a partially schematic, cross-sectional side elevation view of a percutaneous apparatus having a housing with a flexible support surface configured in accordance with another embodiment of the invention.

DETAILED DESCRIPTION

Figure 2A:
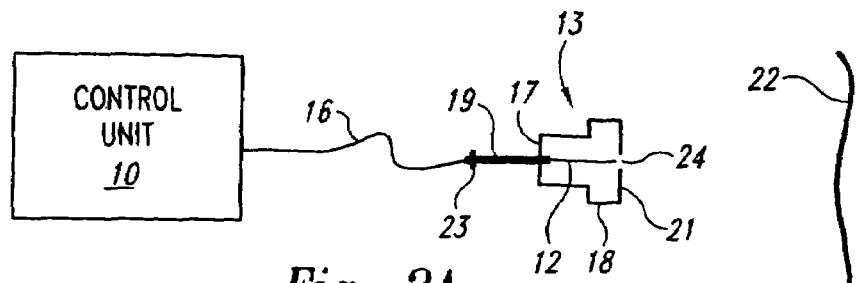
FIGS. 2A-E are schematic illustrations of a percutaneous electrical therapy system according to another embodiment of the invention.

Percutaneous electrical therapy systems, such as PNT systems, deliver electric current to a region of a patient's tissue through electrodes that pierce the skin covering the tissue. The electric current is generated by a control unit external to the patient and typically has particular waveform characteristics such as frequency, amplitude and pulse width. Depending on the treatment or therapy being delivered, there may be one electrode containing both a cathode and an anode or a plurality of electrodes with at least one serving as a cathode and at least one serving as an anode.

The electrode has a sharp point to facilitate insertion through the patient's skin and to enhance local current density during treatment. Once inserted into the skin, the sharp point may become exposed to pathogens, microbes, toxins, etc., in the patient's tissue and/or blood. After removal of the electrode from the patient's tissue, a caregiver or other bystander may be stuck accidentally with the sharp point of the electrode, thereby exposing the caregiver to any pathogens that may be on the used electrode. Aspects of this invention therefore provide a sharp point protection assembly for a percutaneous electrical therapy system.

FIGS. 1A-G are block diagrams showing deployment and use of one embodiment of a percutaneous electrical therapy system and electrode assembly invention. As shown in FIGS. 1A and 1B, the system includes a percutaneous probe, such as an electrode 1 having a sharp point 2 at its distal end and a sharp point protection assembly 3 surrounding at least the electrode's sharp point 2 when the electrode is in its undeployed and uninserted states. The undeployed and uninserted states include pre-deployment and post-deployment states of the electrode. In the embodiment, sharp point protection assembly 3 includes a housing 4 having an aperture 5 at its distal end. An actuator 6 interacts with a handle 11 at the proximal end of electrode 1 as shown.

Deployment of the electrode assembly includes the steps taken to place the electrode assembly in proper position and condition for use in electrical therapy. FIG. 1A shows the electrode assembly in an undeployed (pre-deployed) state. During deployment, the aperture 5 is placed against a patient's skin 22, as shown in FIG. 1B. The electrode 1 is then inserted into the tissue underlying the patient's skin by moving the actuator 6 distally, as shown in FIG. 1C. The actuator 6 may have an optional limit stop element 9 cooperating with a limit stop area 8 of the housing 4 to limit distal motion of the actuator 6 and to control the depth of insertion of the sharp point 2 of the electrode 1. In a preferred embodiment of the invention, for example, where the electrical therapy system is used to provide percutaneous neuromodulation therapy, the predetermined electrode depth is 3 cm. Other electrode depths may be used, of course, depending on the intended application and therapy.

After insertion, the housing 4 and the actuator 6 (which have heretofore acted as an electrode introducer) are preferably removed, as shown in FIG. 1D. The electrode 1 is connected to a control unit 10 via a conductor or a cable 16. For use with PNT, the control unit 10 preferably supplies a current-regulated and current-balanced waveform with an amplitude of up to approximately 20 mA, frequency between approximately 4 Hz and 50 Hz, and pulse width of between approximately 50 µsec and 1 msec. Other electrical waveforms having other parameters may be used, of course, depending on the therapy to be provided. Also, while FIG. 1E shows only one electrode connected to the control unit, it should be understood that a plurality of electrodes may be connected to a single control unit, as called for by the desired electrical stimulation treatment.

After completion of the electrical therapy, the electrode assembly is undeployed. During undeployment, the electrode must be removed from the patient in a sharps-safe manner. In that embodiment, as shown in FIG. 1F, the aperture 5 of the housing 4 of a sharp point protection assembly 3 is placed over the handle portion 11 of the electrode 1. The sharp point protection assembly 3 may be the same assembly used to deploy and insert the electrode (i.e., the electrode introducer), or it may be an entirely different assembly (e.g., an electrode remover). The sharp point 2 of electrode 1 is then drawn into the housing 4 of the sharp point protection assembly 3 by moving the actuator 6 proximally, as shown in FIG. 1G. Thus, the sharp point protection assembly 3 of FIGS. 1A-G helps prevent all unintended contact between the electrode's sharp point and a caregiver or other bystander before, during and after deployment of the electrode.

FIGS. 2A-E are block diagrams of another embodiment of the percutaneous electrical therapy system and electrode assembly invention. A control unit 10 is connected to an electrode 12 within an electrode assembly 13 via a conductor 16. As above, for use with PNT, the control unit 10 preferably supplies a current-regulated and current-balanced waveform with an amplitude of up to approximately 20 mA, frequency between approximately 4 Hz and 50 Hz, and pulse width of between approximately 50 µsec and 1 msec. As shown in its undeployed state in FIG. 2A and in its uninserted state in FIG. 2B, the system includes a sharp point protection assembly 14 comprising a housing 18 surrounding the sharp point 20 of electrode 12 when the electrode point 20 has not yet been inserted through the patient's skin 22.

Figure 2B:
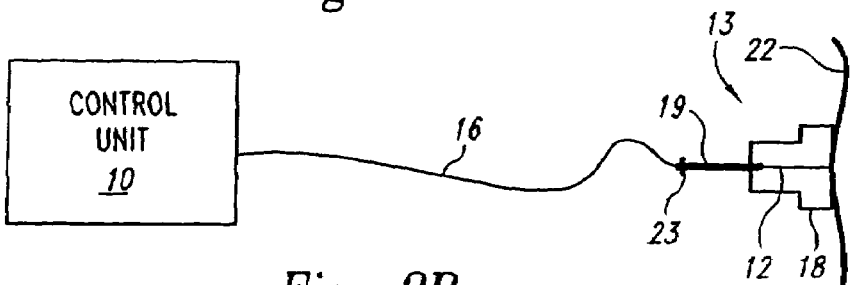
Figure 2C:
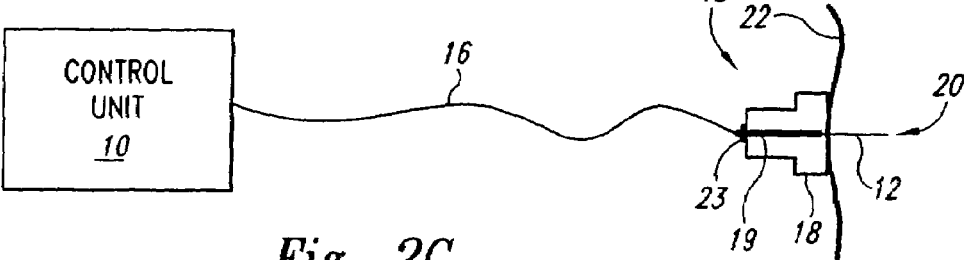

To begin deployment, distal face 21 of a housing 18 is placed against the patient's skin 22, as shown in FIG. 2B. The system may also include an electrode actuator 19 that enables deployment and insertion of the sharp point 20 of electrode 12 through the patient's skin 22 into the underlying tissue to a predetermined depth through an aperture 24 in housing 18, as shown in FIG. 2C. The actuator 19 may be part of the electrode assembly 13 or a separate component of the system. The actuator may have an optional limit stop element 23 that cooperates with a limit stop area 17 of the housing 18 to limit distal movement of the actuator 19, thereby controlling depth of insertion of electrode 12. In a preferred embodiment of the invention, for example, where the electrical stimulation system is used to provide percutaneous neuromodulation therapy, the predetermined electrode depth is approximately 3 cm., although other electrode depths may be used depending on the application. The control unit 10 may then provide the appropriate therapy to the patient through electrode 12 and any other electrodes connected to it.

Figure 2D:
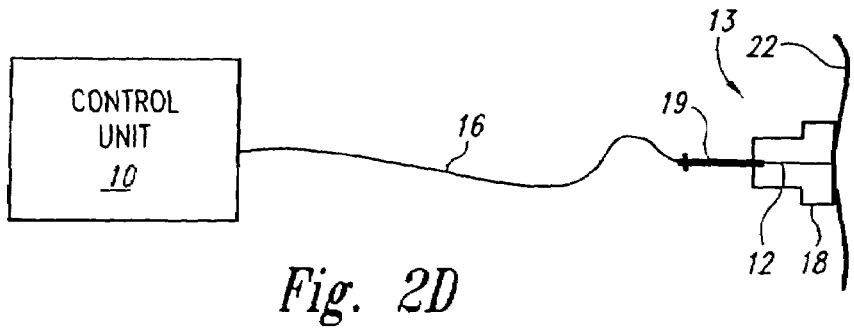
Figure 2E:
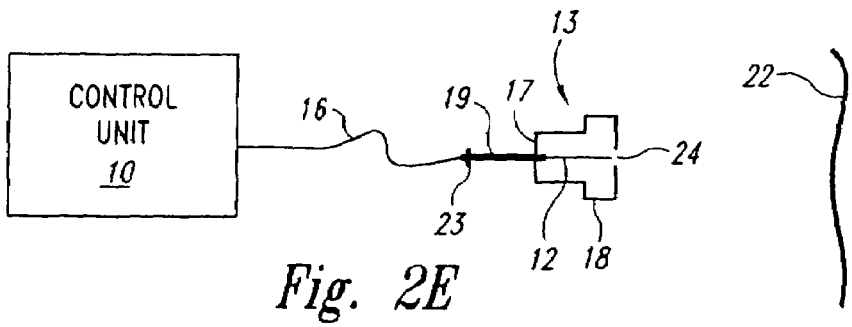

During undeployment, actuator 19 is used to draw electrode 12 back proximally into housing 18. After removal of the electrode from the patient's skin, the housing 18 of the sharp point protection assembly 14 once again surrounds the sharp point 20 of the now uninserted electrode 12, as shown in FIGS. 2D and 2E. The actuator 19 assists in the operation without ever exposing the sharp point of the electrode when the sharp point is no longer in the patient. In fact, the operator of the electrode assembly never sees the sharp point of the electrode. Thus, the sharp point protection assembly 14 shields the potentially contaminated portion of the undeployed electrode and protects the patient's caregiver or other bystander from unintended contact with the sharp point of the electrode before, during and after electrical therapy.

While FIGS. 2A-E show the electrode connected to the control unit prior to deployment and insertion of the electrode into the patient's skin, the connection between the control unit and the electrode could be made during deployment or after insertion. Also, while FIGS. 2A-E show only one electrode connected to the control unit, it should be understood that a plurality of electrodes may be connected to a single control unit, as called for by the desired electrical stimulation treatment.

Figure 3:
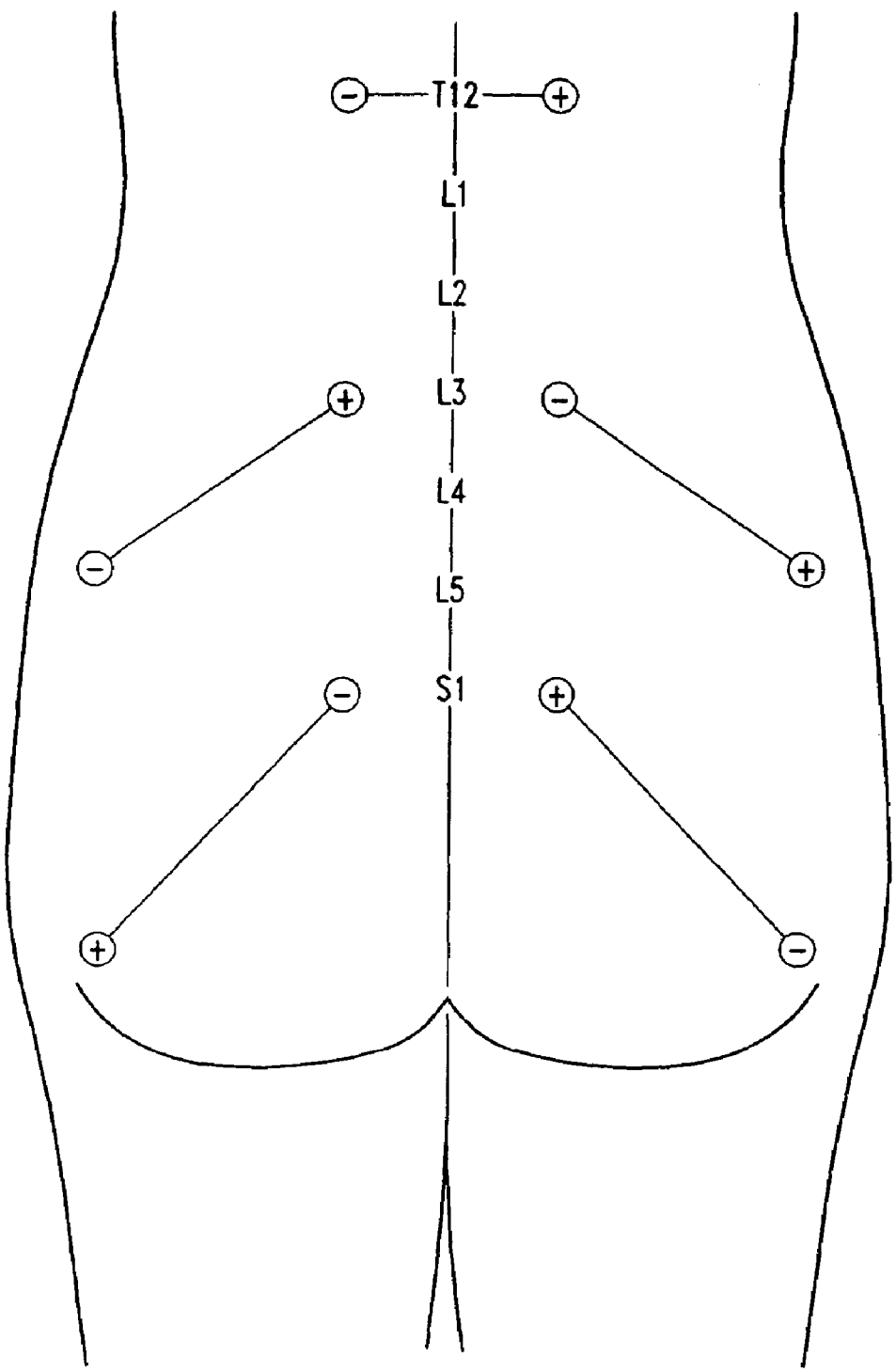
FIG. 3 shows an electrode montage for use in percutaneous neuromodulation therapy to treat low back pain.

To use the percutaneous electrical therapy systems of FIGS. 1A-G and FIGS. 2A-E to treat a patient, one or more electrodes are inserted through the patient's skin into the underlying tissue. As an example, to treat low back pain using PNT with unipolar electrodes, an array or montage such as that shown in FIG. 3 may be used. The "T12" "S1" designations refer to the patient's vertebrae. The sharp point protection assembly shields the electrode assembly operator from exposure to the electrode's sharp point prior to, during and after treatment. The control unit or generator supplies current pulses between pairs of electrodes for durations of a few minutes to several hours, preferably delivering the current-regulated waveform described above. Thirty-minute treatments are recommended in the Ghoname et al. low back pain treatment articles.

During deployment and treatment, the electrode assembly and other parts of the system perform other functions in addition to being a sharps-protected conduit for current flow into the patient. For example, in the embodiment of FIGS. 2A-E, aperture 24, distal face 21 and the interaction of actuator 19 and housing 18 cooperate as an electrode angle of entry controller to control the electrode's entry angle during insertion of the sharp point of the electrode into the patient's tissue. The interaction of the aperture 5, the distal face 7 of the housing 4, and the interaction of the actuator 6 and the housing 4 perform that function in the embodiment of FIGS. 1A-G.

Additional optional details of the electrode assembly may be found in the following concurrently filed and commonly owned U.S. patent applications, the disclosures of which are incorporated herein by reference: Bishay et al., "Percutaneous Electrical Therapy System With Electrode Entry Angle Control;" Leonard et al., "Percutaneous Electrical Therapy System Providing Electrode Axial Support;" Leonard et al., "Percutaneous Electrical Therapy System With Electrode Depth Control;" Leonard et al., "Percutaneous Electrical Therapy System With Electrode Position Maintenance;" Leonard et al., "Electrode Introducer For A Percutaneous Electrical Therapy System;" Bishay et al., "Percutaneous Electrical Therapy System For Minimizing Electrode Insertion Discomfort;" Bishay et al., "Electrode Assembly For A Percutaneous Electrical Therapy System;" and Leonard et al., "Electrode Remover For A Percutaneous Electrical Therapy System."

FIGS. 4-12 show another embodiment of the invention. An electrode assembly 30 includes a base 32, an electrode 34, and a plunger or actuator 36. Base 32 has a flange or flared end 44 that is adapted to make contact with a patient's skin. The base 32 may be formed from any suitable polymer or metal, such as a high density polyethylene (HDPE). The base 32 is preferably opaque so that the electrode cannot be seen by a needle-shy patient.

The actuator 36 fits within a housing portion 40 of the base 32 in a slidable arrangement. A locking assembly is operable to prevent relative movement between the actuator 36 and the housing portion 40 of the base 32. In the embodiment, the locking assembly of the actuator 36 has integrally-formed resilient detents 48 on its exterior cylindrical surface. In the undeployed state of the electrode assembly 30, the detents 48 mate with corresponding openings 50 in the base 32 to hold the actuator 36 and the base 32 in place with respect to each other to prevent electrode 34 from moving outside of the protective housing 40 of the base 32 and thereby providing sharp point protection, as explained further below. Mechanisms other than the detent and opening arrangement shown here may be used to hold the actuator and base in place without departing from the invention.

In the embodiment, the electrode 34 is preferably a 3 cm. long 32 gauge stainless steel needle. Other sizes and materials may be used for the electrode 34, of course, without departing from the scope of the invention. The actuator 36 is preferably formed from HDPE as well, although other suitable materials may be used.

Figure 7:
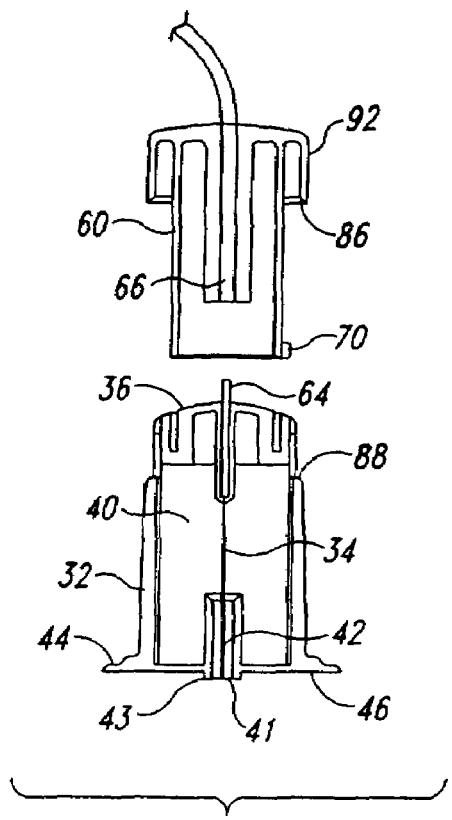
FIG. 7 is a sectional view of the embodiment of FIG. 4 showing the electrode and sharp point protection assemblies and an actuator tool.
Figure 8:
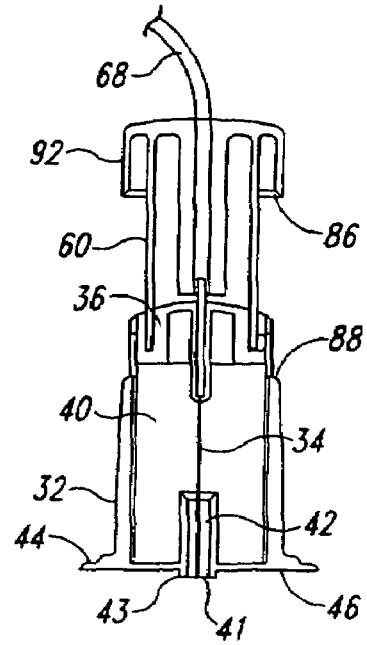
FIG. 8 is a sectional view of the embodiment of FIG. 4 showing the actuator tool in engagement with the electrode and sharp point protection assemblies prior to insertion of the electrode into a patient's tissue.
Figure 9:
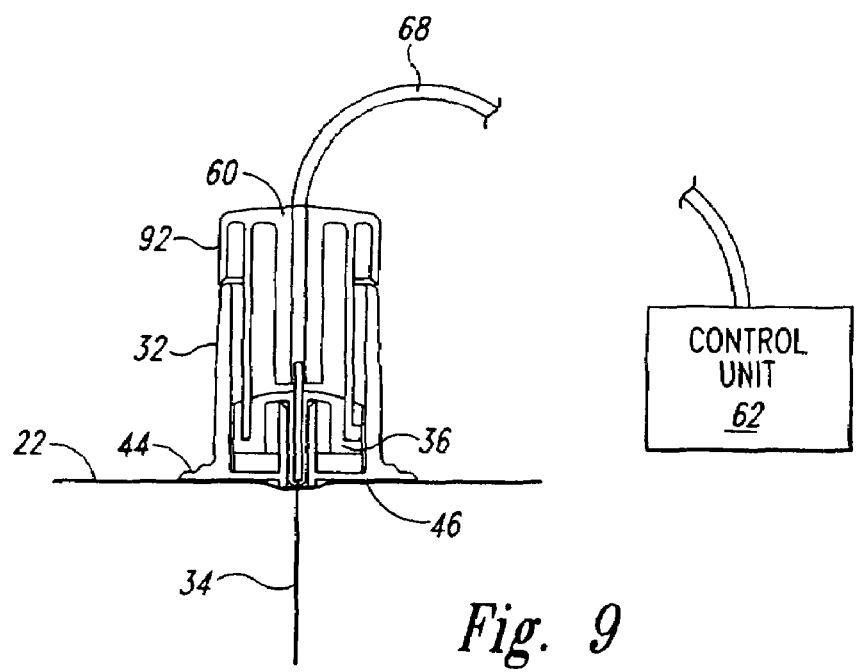
FIG. 9 is a sectional view of the embodiment of FIG. 4 with the electrode in its deployed and inserted state.

The electrode 34 has a larger-diameter handle 52 at its proximal end. The handle 52 fits within a channel 54 formed within actuator 36. Channel 54 has a narrow opening 56 at its distal end whose diameter is slightly larger than the diameter of the electrode 34 but narrower than the diameter of the handle 52 to hold the electrode 34 in place within the actuator 36 after initial manufacture and assembly. As shown in FIG. 7, in an undeployed state the sharp point 38 of the electrode 34 is disposed within the housing portion 40 of base 32, specifically, within a narrow channel 42 of the housing 40.

To deploy one or more electrode assemblies on a patient in order to provide electrical stimulation therapy (such as PNT), the distal surface 46 of a flange portion 44 of the base 32 is mounted on the desired site on the patient's skin, preferably with a compressible adhesive pad (not shown) surrounding a ring 43 extending downward from the surface 46 around an aperture 41 formed at the distal end of the channel 42, although other means of attaching base 32 to the patient may be used as appropriate.

An electrical connector and an actuator tool 60 are used to insert the electrode and connect the electrode electrically with a control unit 62. The actuator tool 60 and the electrode assembly 30 also interact to provide the sharp point protection assembly of the embodiment. When the distal end of the actuator tool 60 is placed against the proximal ends of the base 32 and the actuator 36, the exposed proximal end 64 of the electrode handle 52 makes electrical contact with a contact surface 66 within the actuator tool 60. A contact surface 66, in turn, is electrically connected to the control unit 62 via a cable or other conductor 68.

The actuator tool 60 has two oppositely disposed pegs 70 extending outward from the distal portion of its cylindrically surface. The pegs 70 mate with two corresponding slots 72 in the actuator 36 and with two corresponding grooves 74 in the base 32. (The second slot 72 and the second groove 74 are each opposite the slot 72 and the groove 74, respectively, shown in FIGS. 4 and 5.) When connecting the actuator tool 60 to the electrode assembly 30, the pegs 70 move along longitudinal portions 76 of the slots 72 and along longitudinal portions 78 of the grooves 74. Concurrently, exposed distal end 64 of the electrode handle 52 begins to make sliding contact with the contact surface 66 of the actuator tool 60 to create the electrical connection between the actuator tool 60 and the electrode 32.

Clockwise rotation (looking down on the assembly) of the actuator tool 60 after the pegs 70 reach the end of the longitudinal portions 76 and 78 moves the pegs 70 into short circumferential portions 80 and 82, respectively, of the slots 72 and the grooves 74. The length of the circumferential portions 80 of the slots 72 is less than the length of the circumferential portions 82 of the grooves 74. Continued movement of the pegs 70 along the circumferential portions 82 will therefore move the pegs 70 against the ends 81 of the circumferential slots 80. Further clockwise rotation of the actuator tool 60 will cause the actuator 36 to rotate clockwise as well, thereby moving the detents 48 out of openings 50 and allowing the electrode 34 and the actuator 36 to move with respect to the base 32.

Second longitudinal portions 84 of the grooves 74 are formed in the base 32 at the end of circumferential portions 82. Movement of the pegs 70 distally along the longitudinal portions 84 pushes the pegs 70 against the distal edges of the circumferential slot portions 80, thereby moving the actuator 36 and the electrode 34 distally toward the patient's skin 22.

As it moves, the electrode 34 passes through the channel 42, and the sharp point of the electrode 34 moves out through the aperture 41. The channel 42 and the actuator 36 provide axial support to the electrode 34 during forward movement and also, along with the support provided by flange 44, provide entry angle guidance to the electrode. In addition, downward pressure on the patient's skin during electrode deployment compresses the compressible adhesive pad and presses a ring 43 against the patient's skin 22, which helps ease electrode entry through the skin and also lessens the insertion pain experienced by the patient.

Distal movement of the electrode and its actuator within the base 32 continues until the distal surface 86 of a cylindrical cap portion 92 of the actuator tool 60 meets an annular surface 88 of the housing 40. At this point, a sharp point 38 of the electrode 34 has extended a predetermined depth into the tissue underlying the patient's skin. In the preferred embodiment, this predetermined depth is approximately 3 cm., although other electrode depths may be desired depending on the treatment to be performed.

An optional feature of the invention is a deployed electrode holding mechanism. In the embodiment, an interference fit between the inner surface of the channel 42 and the outer surface 55 of the channel 52 performs this function.

Electrical stimulation treatment may begin once the electrodes have been deployed and inserted. A control unit 62 supplies stimulation current to the electrodes, e.g., in the manner described in the Ghoname et al. articles. The electrical waveform provided by the control unit depends on the application. For example, in an embodiment of a system providing percutaneous neuromodulation therapy, control unit 62 would preferably provide a current-regulated and current-balanced waveform with an amplitude of up to approximately 20 mA, frequency between approximately 4 Hz and 50 Hz, and pulse width of between approximately 50 μsec and 1 msec.

The interaction of the actuator tool 60 and the base 32 provides stability to the electrode 34 and its electrical connection to the control unit during treatment by holding the electrode in place, by providing strain relief for tugging forces on the cable 68, and by providing a robust mechanical connection. It should be noted that the sharp point of the electrode is not exposed to the operator or to any other bystander at any point during deployment and use of the electrode assembly.

After treatment has been completed, the electrode may be removed from the patient. To do so, the actuator tool 60 is moved proximally away from the patient. As the pegs 70 move proximally along the longitudinal portions 84 of the grooves 74, the pegs 70 push against proximal edges of the actuator's circumferential slot portions 80, thereby moving the actuator 36 and the electrode 34 proximally as well. When the pegs reach the proximal end of the longitudinal groove portions 84, the sharp end 38 of the electrode 34 is out of the patient and safely inside the housing 40 of the base 32. Counterclockwise movement of the actuator tool 60 moves pegs along the circumferential portions 80 and 82 of the slot 72 and the groove 74, respectively. Since, as discussed above, the circumferential portion 80 is shorter than the circumferential portion 82, that counterclockwise movement will turn the actuator 36 counterclockwise.

At the limit of the counterclockwise movement, the detents 48 move back into the openings 50 to prevent further movement of the electrode and actuator with respect to the base 32. Further distal movement of the actuator tool 60 moves the pegs 70 distally along the longitudinal portions 76 and 78 of the slot 72 and the groove 74, respectively, to disconnect actuator tool 60 from the electrode assembly 30. The base 32 can then be removed from the patient.

Once again, at no time during the electrode deployment, use or removal processes was the sharp point of the electrode exposed to the operator or bystanders.

Figure 10:
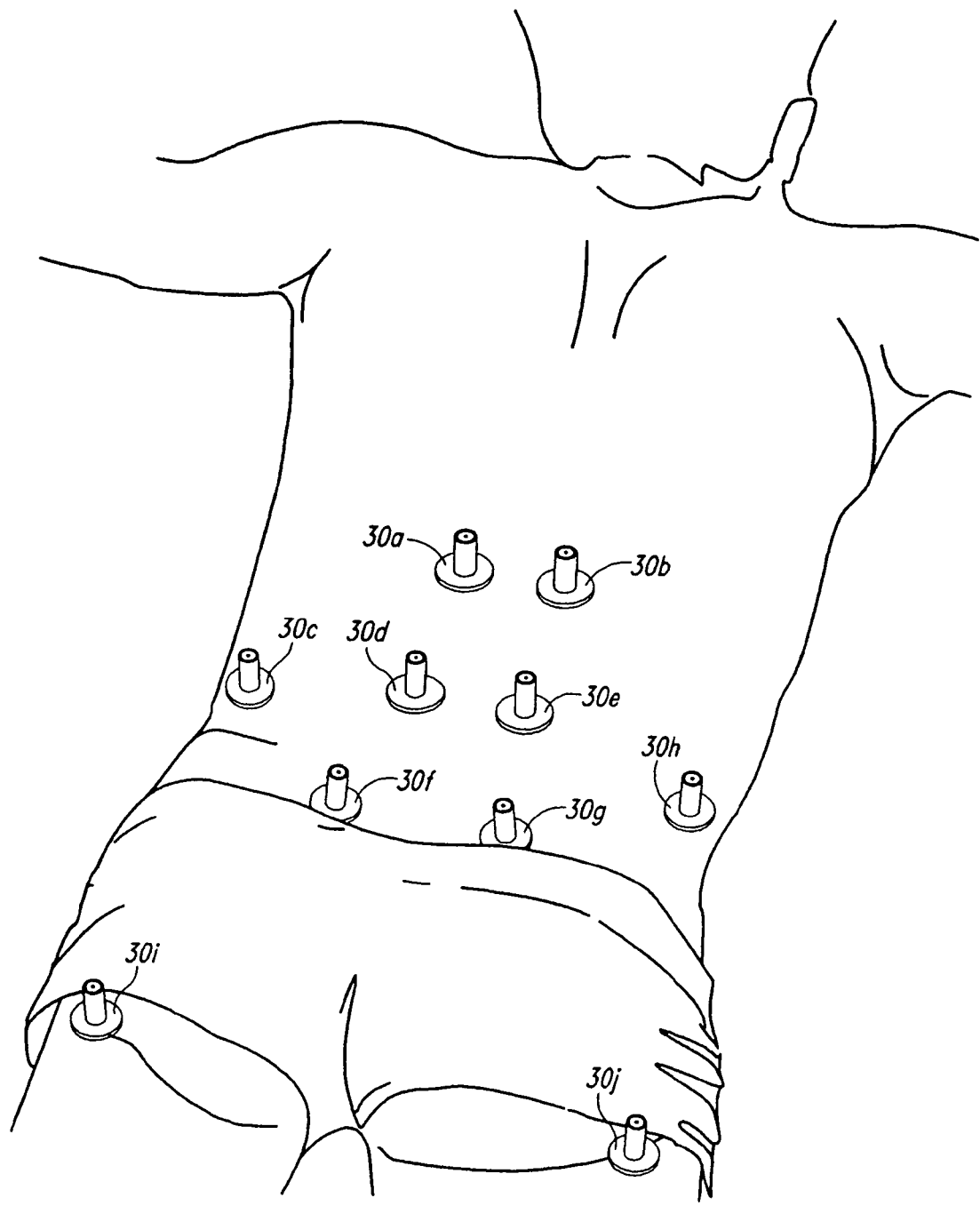
FIG. 10 shows a montage for using the embodiment of FIG. 4 to treat low back pain with the electrodes in a partially deployed but uninserted state.
Figure 11:
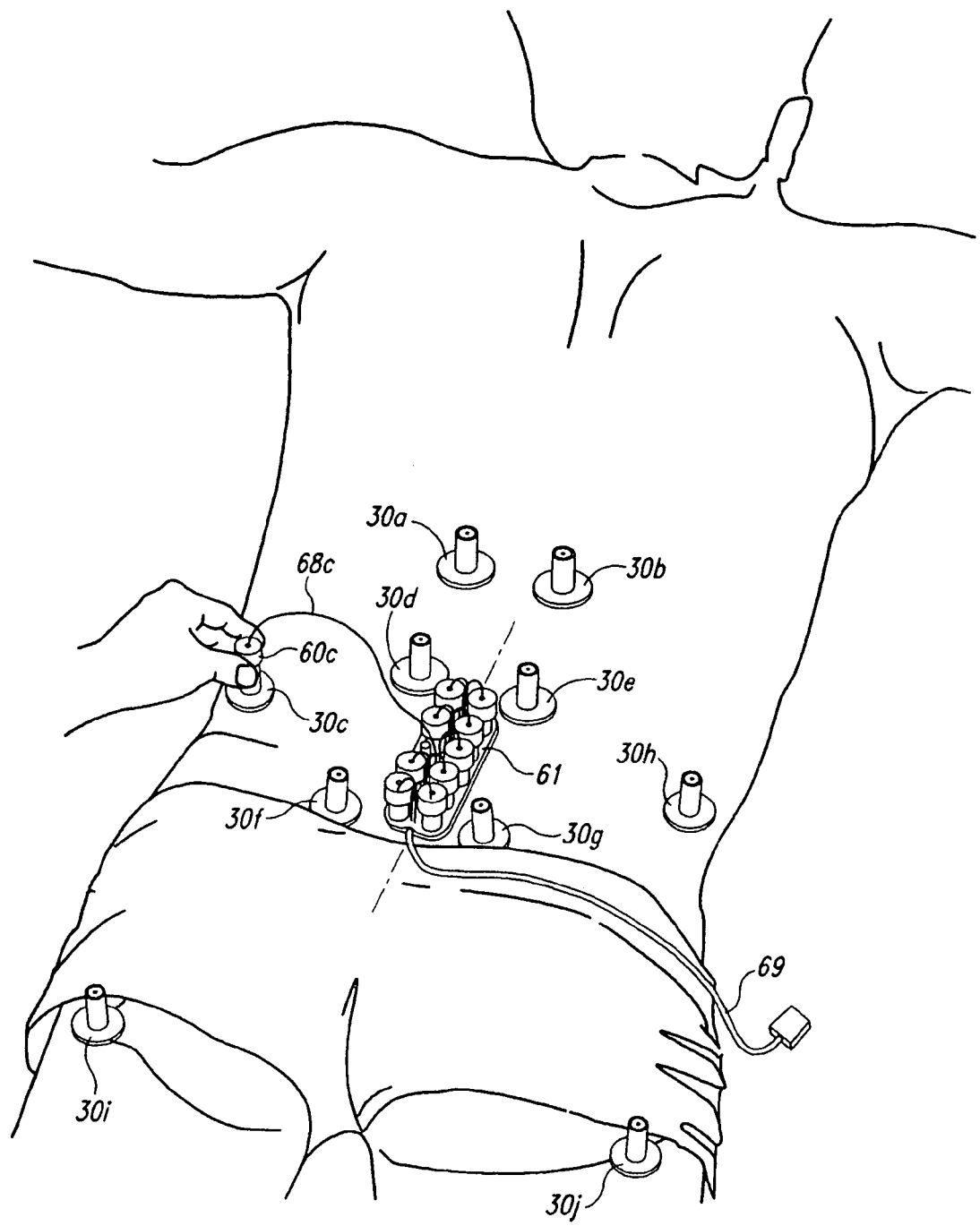
FIG. 11 shows the electrode montage of FIG. 10 at the beginning of the electrode insertion step.
Figure 12:
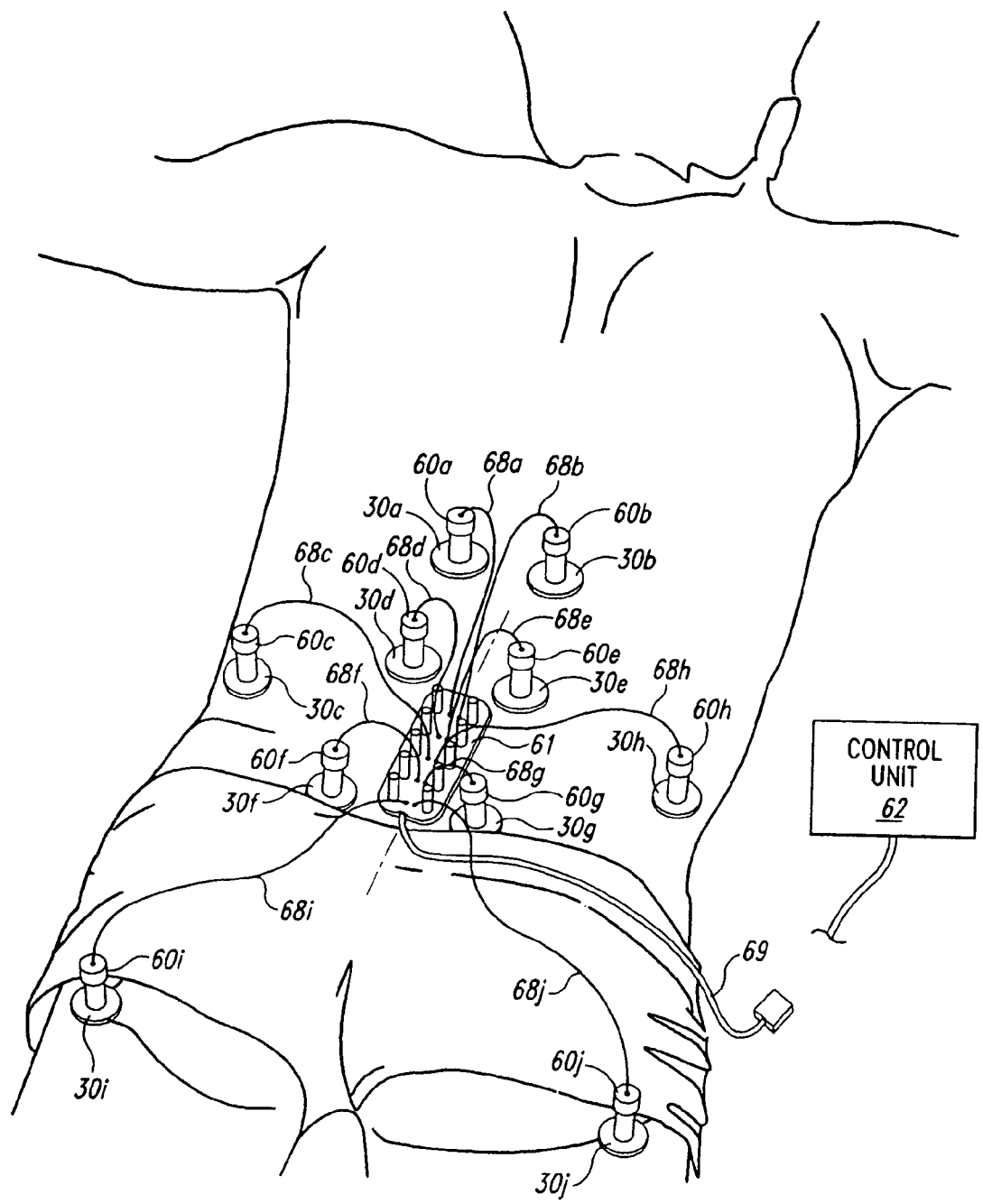
FIG. 12 shows the electrode montage of FIG. 10 with the electrodes deployed, inserted and attached to a control unit to provide electrical therapy to the patient.
Figure 13:
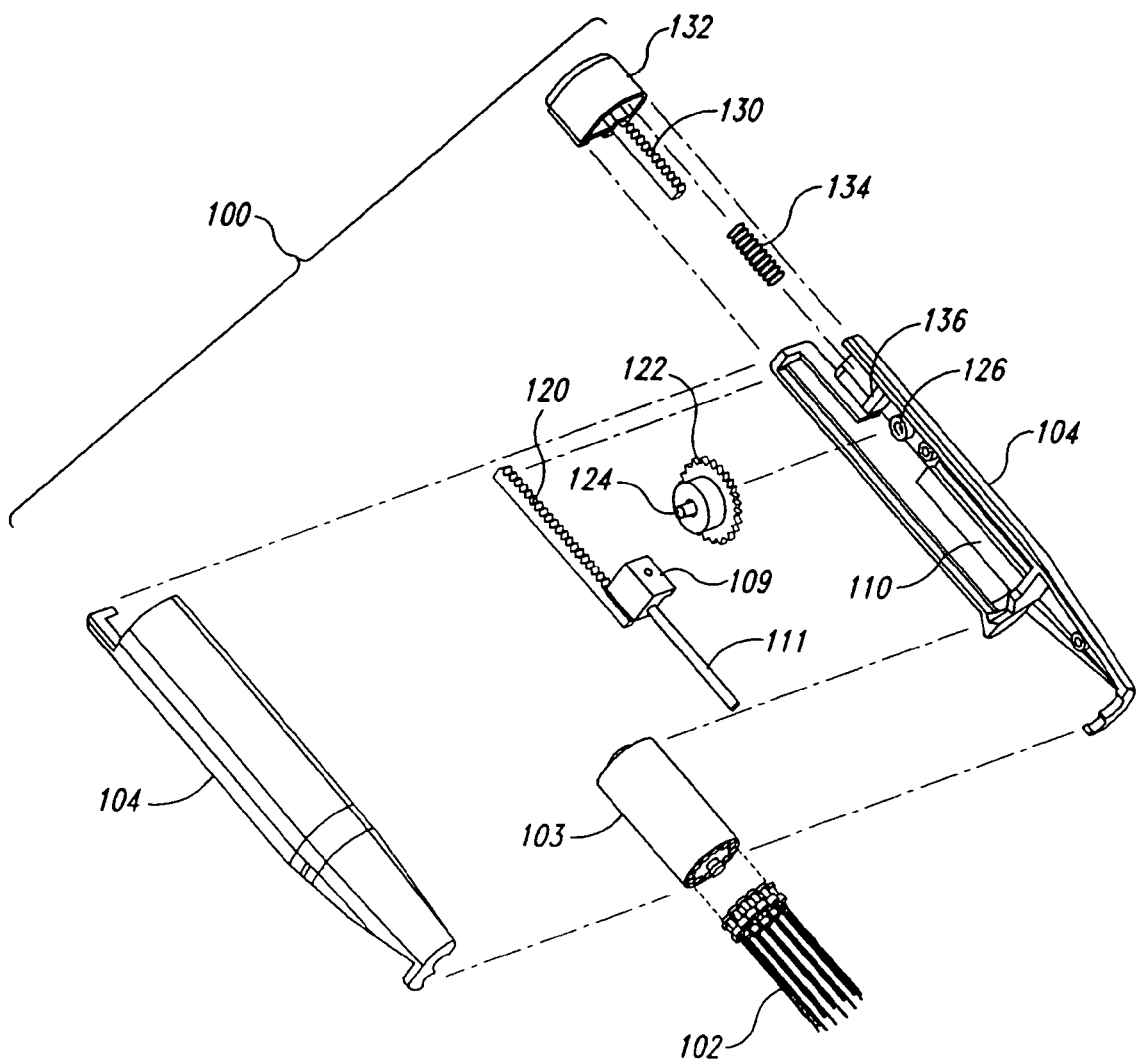
FIG. 13 is an exploded view of an electrode introducer and sharp point protection assembly of yet another embodiment of the invention.

FIGS. 10-12 show the use of the electrode and sharp point protection assemblies of FIGS. 4-9 to treat low back pain using PNT. As shown in FIG. 10, ten electrode assemblies 30a-j are arranged in a montage on the patient's back and attached with adhesive. Next, ten actuator tools 60a-j are attached to the ten electrode assemblies 30a-j. In this example, prior to deployment the actuator tools are mounted on an actuator tool tray 61 that provides electrical communication to the control unit 62 via the cable 69. The actuator tools electrically connect with the tool tray 61, and thereby to the cable 69 and the control unit 62, via individual cables 68a-j. FIG. 11 shows the beginning of the electrode insertion process.

Once each electrode assembly has been actuated by its respective actuator tool to insert an electrode into the patient's tissue (as shown in FIG. 12), the control unit 62 provides electrical signals to treat the patient. Preferably, half the electrodes (e.g., assemblies 30b, 30d, 30g, 30h and 30i) are treated as anodes, and the other half as cathodes. In the preferred embodiment, the control unit 62 would provide a current-regulated and current-balanced waveform with an amplitude of up to approximately 20 mA, frequency between approximately 4 Hz and 50 Hz, and pulse width of between approximately 50 μsec and 1 msec. to treat the patient's low back pain using PNT.

Another embodiment of the invention is shown in FIGS. 13-28. In the embodiment, an electrode introducer and an electrode remover cooperate to provide sharp point protection.

In one embodiment, an electrode introducer 100 is shown in FIGS. 13-16 and 19-21. In the embodiment, an introducer 100 is designed to insert multiple electrodes. It should be understood that the principles of the invention could be applied to an introducer designed to hold and insert any number of electrodes.

Twelve electrodes 102 are disposed within a magazine 103 rotatably mounted within a housing 104. In the embodiment, the housing 104 is a two-part injection molded polystyrene assembly. As seen best in FIG. 14, the magazine 103 rotates about a hub 105 mounted on supports formed in the housing 104. A leaf spring 106 mates with one of twelve radial grooves 108 formed in the magazine 103 to form a twelve-position ratchet mechanism for the rotatable magazine 103 in the housing 104.

Figure 14:
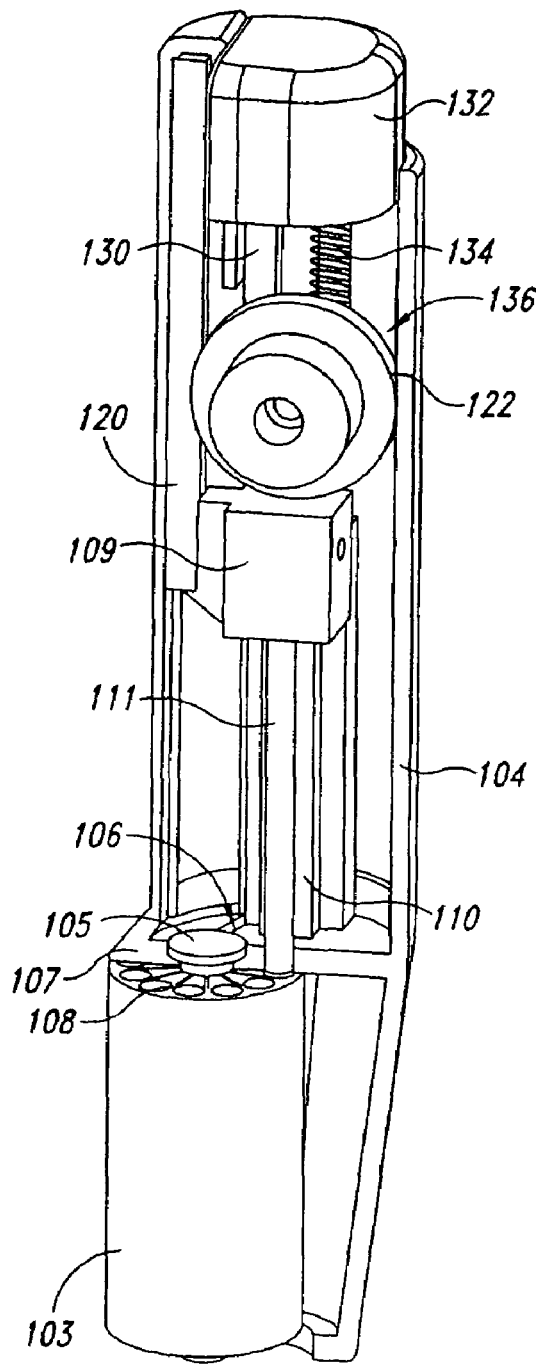
FIG. 14 is a partial sectional view of the introducer and sharp point protection assembly of FIG. 13.
Figure 15:
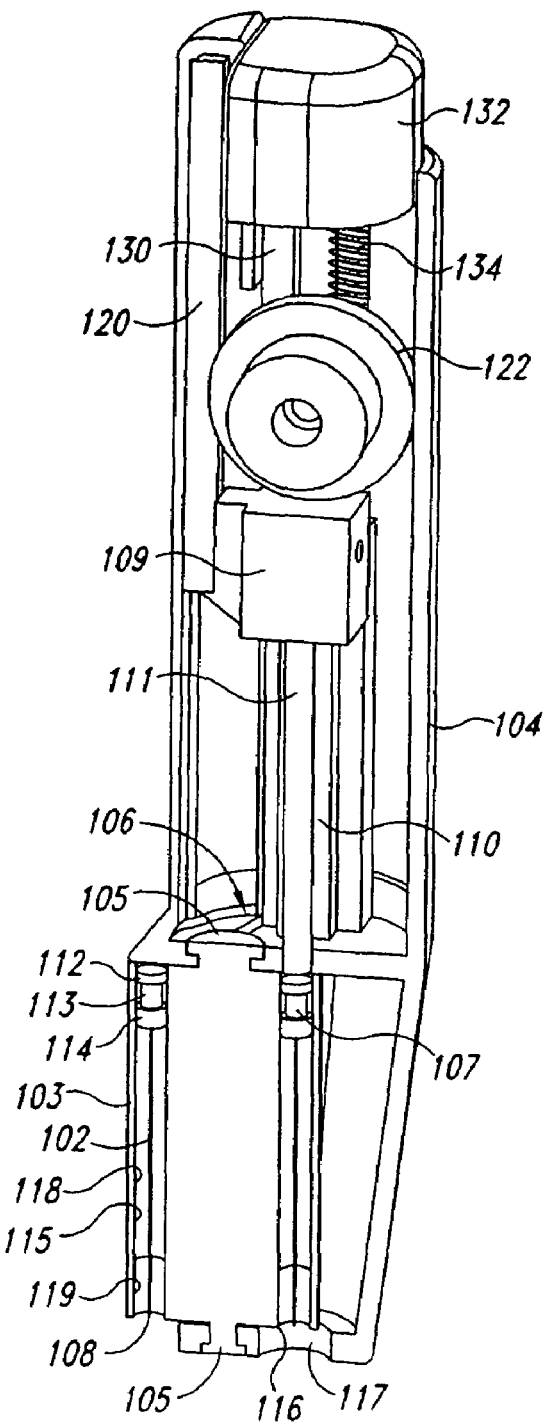
FIG. 15 is a sectional view of the introducer and sharp point protection assembly of FIG. 13.
Figure 16:
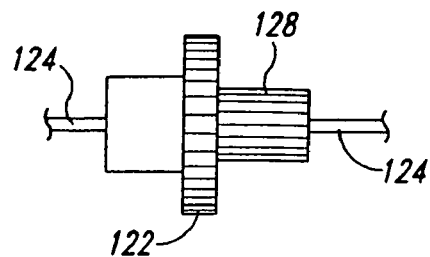
FIG. 16 is an elevational view of gear assemblies of the introducer and sharp point protection assembly of FIG. 13.

The magazine 103 has twelve electrode chambers 115 arranged radially about hub the 105. When the introducer 100 is completely full, each chamber 115 contains one electrode 102. The diameter of an upper portion 118 of the chamber 115 is sized to form an interference fit with the wider portions 112 and 114 of the electrode handle portion 107 of the electrode 102. Lower wide portion 114 of the electrode 102 is formed from a compressible material. The diameter of a lower portion 119 of the chamber 115 is slightly larger so that there is no interference fit between the chamber portion 119 and the electrode handle 107, for reasons explained below. Each time the leaf spring 106 is within a groove 108, the opening 106 of the magazine chamber 115 is lined up with the aperture 117 of the introducer 100, as shown in FIGS. 14 and 15.

A slide member 109 is disposed on a rail 110 formed in the housing 104. Extending longitudinally downward from slide member 109 is a drive rod 111, and extending longitudinally upward from a slide member 109 is a gear rack 120. The teeth of the gear rack 120 cooperate with teeth on a rotational gear 122 mounted about a shaft 124 extending into a shaft mount 126 formed in the housing 104. A second set of teeth are mounted on a smaller diameter rotational gear 128 (shown more clearly in FIG. 16) which is also mounted about the shaft 124. The gears 122 and 128 rotate together about the shaft 124.

The teeth of the smaller diameter gear 128 mesh with the teeth of a second gear rack 130 extending from a longitudinally-movable actuator 132. A spring 134 mounted between the actuator 132 and a spring platform 136 biases the actuator 132 away from the housing 104.

To deploy the electrode assembly of the embodiment, a flexible and compressible annular patch 140 is placed on the patient's skin at the desired site, preferably with adhesive (not shown). For example, to treat low back pain using PNT, the arrangement or montage shown in FIG. 17 may be used. In that montage, five electrodes serve as cathodes and five serve as anodes.

Figure 20:
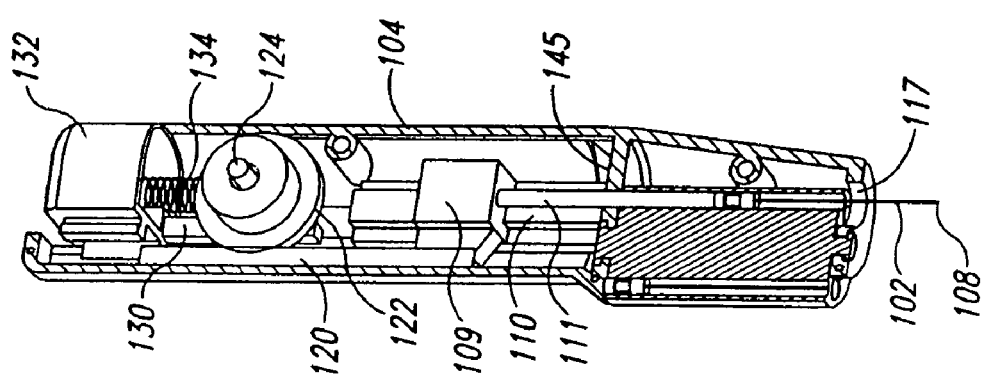
FIG. 20 is a sectional view showing the introducer of FIG. 13 in the process of deploying an electrode, during insertion of the electrode.
Figure 19:
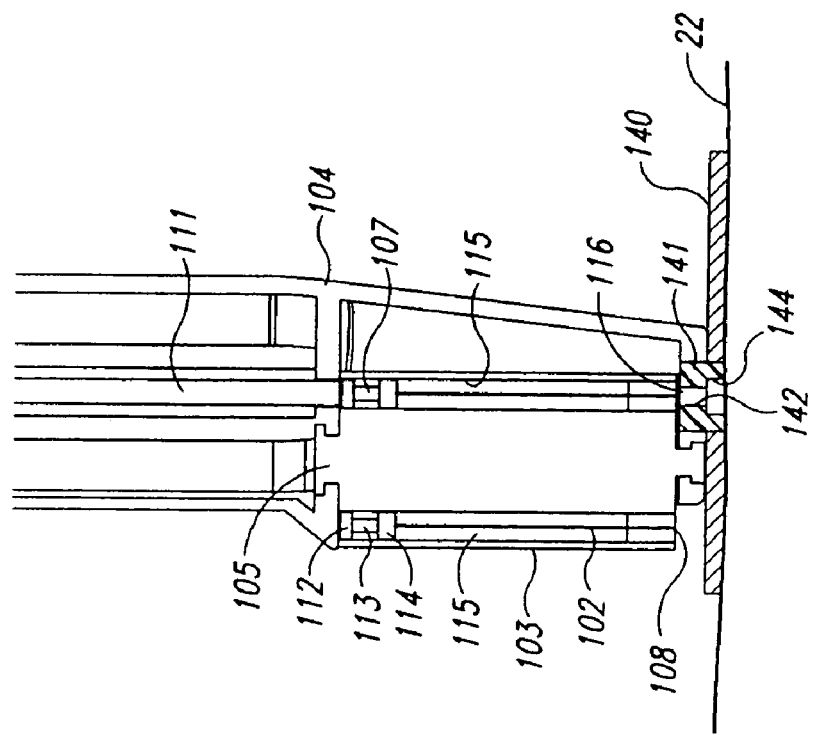
FIG. 19 is a sectional view showing the introducer of FIG. 13 in the process of deploying an electrode, prior to insertion of the electrode.

As shown in FIGS. 19 and 20, patch 140 has an annular rigid member 141 disposed in its center and extending upwardly from it. The rigid member 141 has a smaller diameter opening 142 leading to a larger diameter opening 144. The diameter of the opening 142 is slightly smaller than the lower wide portion 114 of the handle portion 107 of the electrode 102 and slightly larger than the diameter of the central portion 113 of the handle portion 107 of the electrode 102.

Figure 18:
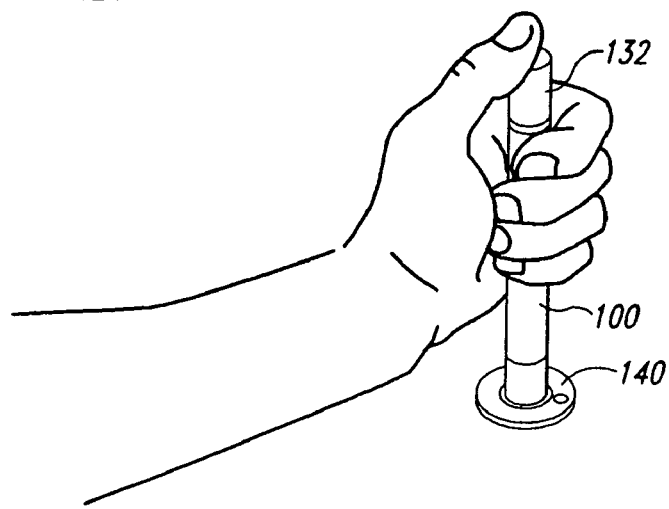
FIG. 18 is an elevational view showing the introducer of FIG. 13 in the process of deploying an electrode.

After the patch 140 is in place, the distal end of introducer 100 is placed against the patch 140 so that an introducer aperture 117 surrounds the upwardly extending portion of the rigid patch member 141, as shown in FIG. 18. That interaction aligns the opening 116 of one of the introducer's magazine chambers 115 with the opening 142 of the rigid member 141 and helps control the electrode's angle of entry, as shown in FIG. 19. Downward pressure on the introducer 100 compresses the patch 140, thereby causing the upper surface of rigid member 141 to engage a lower surface of magazine 103 and pressing rigid member 141 downward into the patient's skin 22. The pressure on the patient's skin around the insertion site minimizes the pain of insertion of the electrode.

Depressing the actuator 132 moves the gear rack 130 distally, which causes the gears 128 and 122 to rotate. Because of the relative diameters and relative tooth counts of the gears 128 and 122, the gear rack 120 moves longitudinally a much greater distance than the corresponding longitudinal movement of the gear rack 130. That feature enables the electrode to be inserted its required distance into the patient's skin using only a comparatively small movement of the operator's thumb. Distal movement of gear rack 120 is guided by the movement of the slide member 109 along the rail 110.

As the slide member 109 moves distally, the drive rod 111 moves into the magazine chamber 115 until the distal end of the drive rod 111 engages the top surface of the electrode's handle portion 107. As shown in FIG. 20, further distal movement of the drive rod 111 pushes the electrode 102 downward so that the sharp point 108 of the electrode 102 leaves the introducer housing and enters the patient's skin 22 and the tissue beneath the skin. The chamber 115 provides axial stability to the electrode 102 during insertion.

When the top portion 112 of the electrode handle portion 107 leaves the smaller diameter portion 118 of the magazine chamber 115, it enters the larger diameter portion 119 of the chamber 115. At that point (shown in FIG. 21), because the diameter of the chamber portion 119 is wider than the diameter of the electrode handle 107, the electrode is no longer attached to the introducer 100.

Continued downward movement of the actuator 132 and the drive rod 111 pushes the lower larger diameter portion 114 of the electrode handle 107 through the smaller diameter portion 142 of the rigid member 141 by compressing the handle portion 114. Further downward movement pushes the handle portion 114 into the larger diameter portion 144 of the rigid member 141 so that the rigid member's smaller diameter portion lies between the larger diameter portions 112 and 114 of the electrode handle 107. That interaction holds the electrode in place in the patient's tissue and helps provide depth control for electrode insertion. In the embodiment, the preferred depth of the electrode's sharp point 108 is approximately 3 cm., although other electrode depths may be desired depending on the treatment to be performed. The slide member 109 also acts as a limit stop at the point when the slide member 109 engages the limit stop area 145 of the housing 104, thereby also controlling electrode insertion depth.

Figure 22:
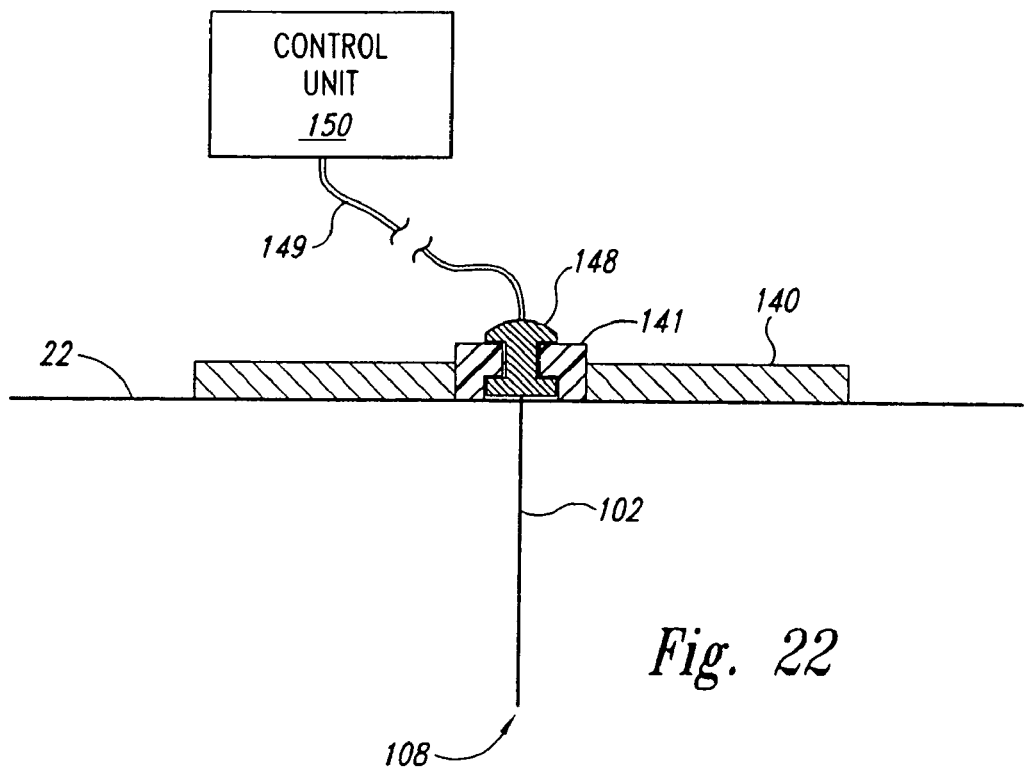
FIG. 22 is a sectional view of an inserted electrode assembly of the embodiment of FIGS. 13-16.
Figure 17:
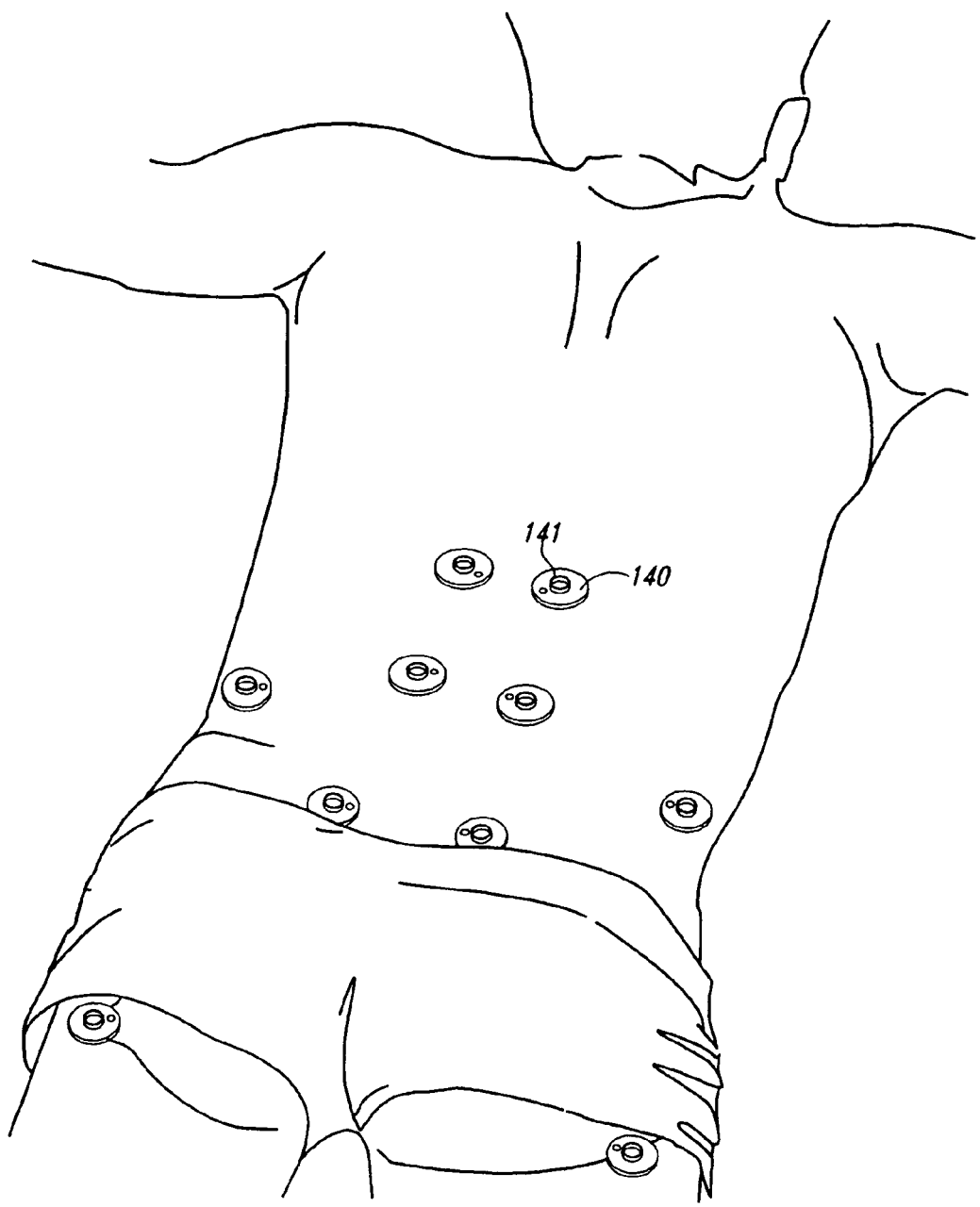
FIG. 17 shows part of the electrode assembly of the embodiment of FIGS. 13-16 in a montage used for treating low back pain using PNT.
Figure 21:
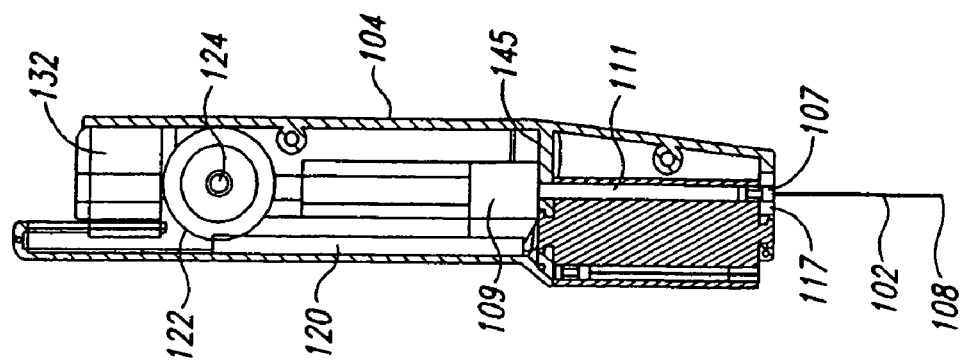
FIG. 21 is a sectional view showing the introducer of FIG. 13 in the process of deploying an electrode, also during insertion of the electrode.

The magazine 103 is rotated to a new insertion position and placed against an empty patch 140 after insertion of each electrode until all electrodes have been deployed and inserted. A suitable electrical connector 148 such as an alligator clip is electrically connected to the electrode 102 through an aperture (not shown) formed in the upper larger diameter portion 112 of the electrode handle 107 to provide electrical communication between a control unit 150 and the electrode 102 via a cable or other conductor 149, as shown in FIG. 22. The patch 140 provides strain relief for the electrode 102 by preventing tugging forces on the cable 149 from dislodging the electrode from the patient, thereby helping keep the electrode in place.

A control unit 150 supplies stimulation current to the electrodes, e.g., in the manner described in the Ghoname et al. articles. Once again, the electrical waveform provided by the control unit depends on the application. For example, in an embodiment of a system providing percutaneous neuromodulation therapy, control unit 150 would preferably provide a current-regulated and current-balanced waveform with an amplitude of up to approximately 20 mA, frequency between approximately 4 Hz and 50 Hz, and pulse width of between approximately 50 μsec and 1 msec.

It should be noted that at no time during the electrode deployment, insertion and electrical therapy treatment processes was the sharp point of the electrode exposed to the operator or bystanders.

In an alternative embodiment, the lower wide portion of the electrode handle is formed from a rigid material and has rounded camming edges. The central annulus of the patch 140 in that alternative embodiment is either compressible or has a resilient camming opening under the camming action of the electrode handle.

In other embodiments, the introducers 100 can have other arrangements. For example, the electrodes 102 can be housed in a magazine having a linear or other non-rotational arrangement. In yet another embodiment, the magazine can house percutaneous probes other than PNT electrodes, either alone or in combination with PNT electrodes. Those other probes can include diagnostic electrical signal receptors, acupuncture needles, and/or hollow fluid delivery/withdrawal needles.

FIGS. 23-28 show a sharps-safe remover according to one embodiment of the invention. A remover 200 is designed to work with the electrode and electrode patch assembly described with respect to FIGS. 13-22 above. It should be understood that the principles of sharps-safe remover 200 may apply to other electrode designs as well.

The remover 200 has a housing 202 with an aperture 204 at its distal end. A number of previously undeployed electrodes 102 are stored within the housing 202. A pair of rails 214 and 216 hold the electrodes 102 in alignment via the electrode handles 107, as shown. While the embodiment of the remover is designed to provide sharps-safe removal and storage of a plurality of electrodes, the invention applies to removers designed to remove and store one or any number of electrodes.

Figure 23:
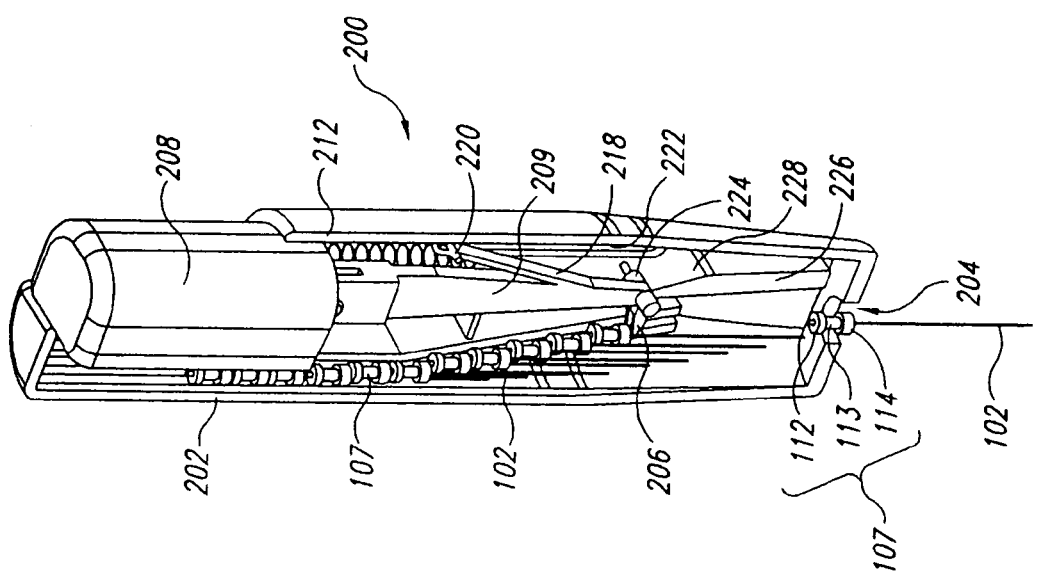
FIG. 23 is a partial sectional view of an electrode remover and sharp point protection assembly according to yet another embodiment of the invention prior to removal of an electrode.

As described above, electrodes for percutaneous electrical therapy are inserted through a patient's skin into underlying tissue with handle portions exposed above the skin. The first step in undeploying and removing an inserted electrode is to line up the exposed handle 107 of an electrode with the remover's aperture 204, as shown in FIG. 23, by placing the distal face 205 of the remover 200 against the patient's skin or against any portion of the electrode assembly (such as an adhesive patch) surrounding the electrode. While not shown in FIGS. 23-28, the aperture 204 is sized to surround an annular member (such as annular member 141 discussed above) holding an electrode handle of an electrode assembly (such as that shown in FIGS. 13-22 above), the sharp point of which has been inserted through a patient's skin.

An electrode engagement fork 206 is pivotably attached to a longitudinally movable actuator 208 via an arm 209 and a hinged pivot 210. A coil spring 212 biases the actuator 208 upwards towards the actuator and fork position shown in FIG. 28. A leaf spring 218 extends from the arm 209. A cross-bar 220 at the end of the leaf spring 218 slides in groove 222 and a corresponding groove (not shown) on the other side of housing 202. Leaf spring 218 is in its relaxed state in the position shown in FIG. 23. In that position, a cross-bar 224 extending from the distal end of the arm 209 adjacent the fork 206 lies at the top of a camming member 226 and a corresponding camming member (not shown) on the other side of the housing 202.

Figure 24:
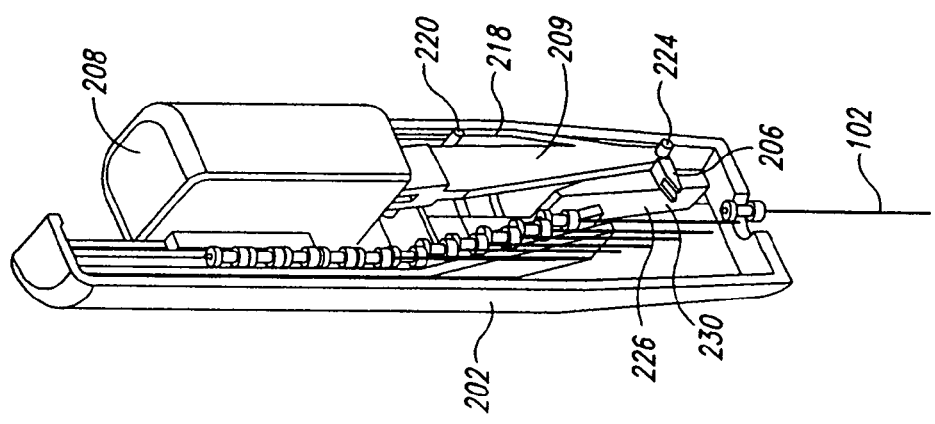
FIG. 24 is a partial sectional view of the electrode remover and sharp point protection assembly of FIG. 23 partially actuated but prior to removal of an electrode.

Downward movement of the actuator 208 (in response, e.g., to pressure from a user's thumb) against the upward force of the spring 212 moves the cross-bar 224 against a first camming surface 228 of the camming member 226, as shown in FIG. 24. The camming surface 228 pushes the cross-bar 224 of the arm 209 against the action of the leaf spring 218 as the actuator 208, the arm 209 and the fork 206 move downward.

Figure 25:
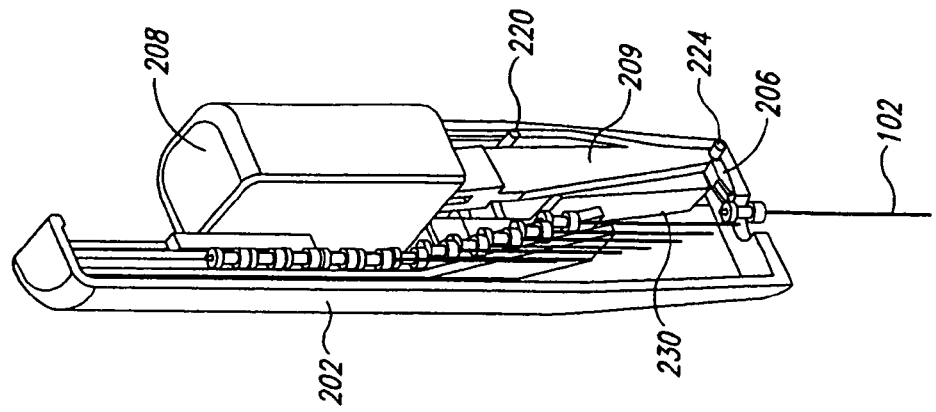
FIG. 25 is a partial sectional view of the electrode remover and sharp point protection assembly of FIG. 23 partially actuated but prior to removal of an electrode.
Figure 26:
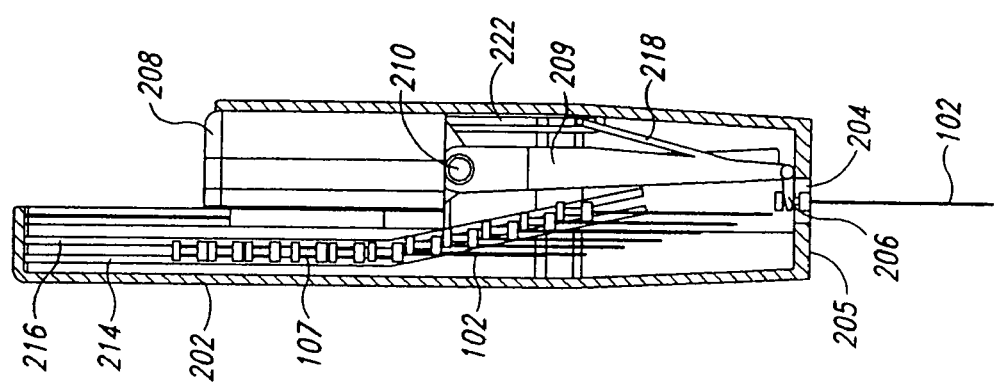
FIG. 26 is a partial sectional view of the electrode remover and sharp point protection assembly of FIG. 23 partially actuated and engaged with an electrode but prior to removal of the electrode.

FIG. 25 shows the limit of the downward movement of the fork 206. At that point, the cross-bar 224 clears the camming member 226, and the leaf spring 218 rotates the fork 206 and the arm 209 about the pivot 210 to engage the fork 206 with the electrode handle 107, as shown in FIG. 26. The tine spacing of fork 206 is shorter than the diameter of the upper wide portion 112 of the electrode handle 107 but wider than the diameter of the narrow middle portion 113 of the electrode handle 107.

Figure 27:
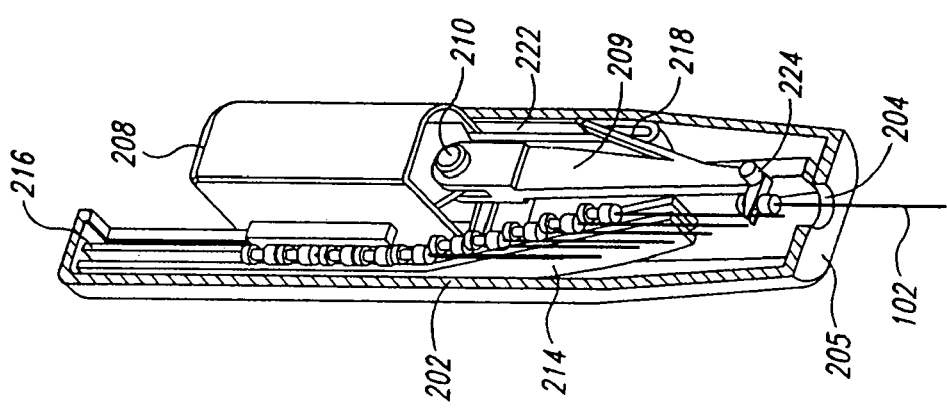
FIG. 27 is a partial sectional view of the electrode remover and sharp point protection assembly of FIG. 23 during removal of an electrode.

Release of the actuator 208 by the user permits the spring 212 to move the actuator 208, the arm 209 and the fork 206 proximally. The engagement between the fork 206 and the electrode handle 107 causes the electrode to begin to move proximally with the fork out of the patient and into the remover housing, as shown in FIG. 27. At this point, the cross-bar 224 is now engaged with a second camming surface 230 of the camming member 226. A camming surface 230 pushes the cross-bar 224 against the action of the leaf spring 218 in the other direction (to the left in the view shown in FIG. 27) as the electrode, the fork and the arm rise under the action of the coil spring 212.

Figure 28:
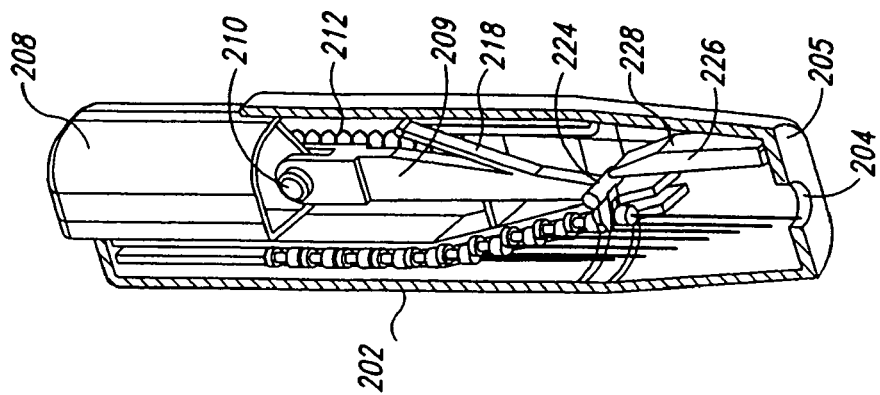
FIG. 28 is a partial sectional view of the electrode remover and sharp point protection assembly of FIG. 23 after removal of an electrode.

The electrode and fork continue to rise until they reach the upward limit of their permitted motion, as shown in FIG. 28. At that point, the electrode handle 107 has engaged the rails 214 and 216 and the most recent electrode previously stored in the remover 200. Electrode handle 107 pushes against the electrode handle of the previously stored electrode handle, which in turn pushes against any electrode handles stored above it in the stack. In this manner, the latest electrode removed by the remover 200 goes into the bottom of the stack of used electrodes stored in remover 200. Now that the sharp point 108 of the electrode 102 is safely inside the housing 202, the remover 200 can be withdrawn from the site on the patient's skin through which the electrode had been inserted. Once the cross-bar 224 clears the top of the camming member 226, and the leaf spring 218 moves the arm 209 back to the center position shown in FIG. 23.

It should be noted that the remover 200 provides sharp point protection for the entire electrode undeployment and removal process. Once all electrodes have been removed, the used electrodes can be safely transported in the sharps-safe container provided by the housing 202 of the remover 200.

Figure 29:
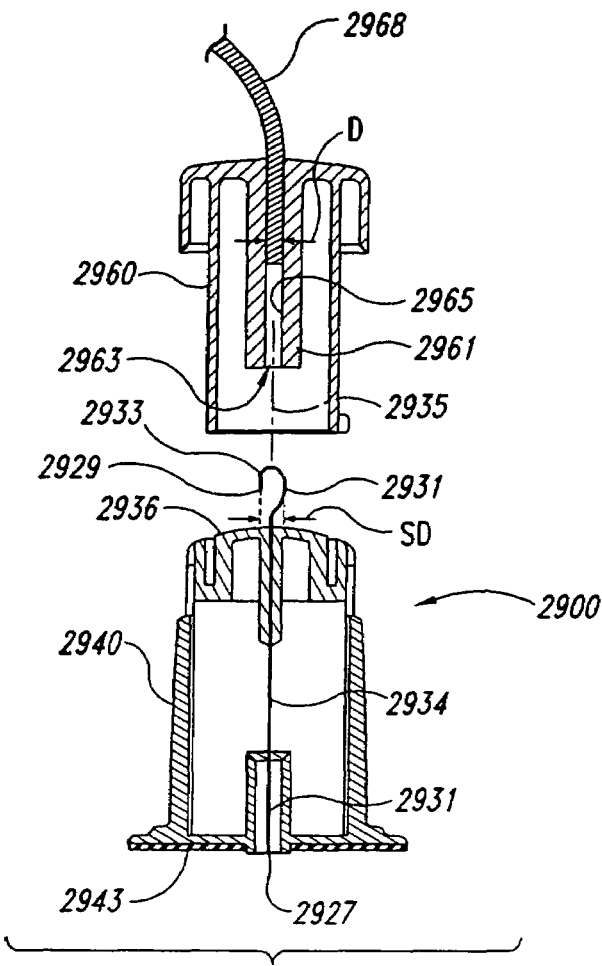
FIG. 29 is a partially schematic, cross-sectional view of an apparatus having a percutaneous probe and a removable coupling member in accordance with an embodiment of the invention.

FIG. 29 is a partially schematic, cross-sectional illustration of an apparatus 2900 having a coupling member 2961 that electrically couples to a percutaneous probe 2934 in accordance with an embodiment of the invention. In one aspect of the embodiment, the percutaneous probe 2934 can include an electrical current-carrying diagnostic and/or therapeutic electrode supported by an actuator 2936, which is movably positioned in a housing 2940. The housing 2940 can include an attachment device 2943 (for example, an adhesive layer or patch) that attaches the housing 2940 to a recipient's skin. The actuator 2936 can move within the housing 2940 to deploy the percutaneous probe 2934 into the recipient's skin in a manner generally similar to that described above with reference to FIGS. 7-9.

The percutaneous probe 2934 can include a first segment 2931 having a sharp first end 2927 which is configured to pass through the recipient's skin. The percutaneous probe 2934 can further include a second segment 2933 having a second end 2929. In one aspect of this embodiment, the first and second segments 2931, 2933 can be portions of a continuous, integrally formed component. In other embodiments, the first and second segments 2931, 2933 can be separately formed and joined together. In any of those embodiments, the percutaneous probe 2934 can be bent, formed, or otherwise configured so that at least part of the first segment 2931 faces toward at least part of the second segment 2933. For example, in one particular embodiment, the percutaneous probe 2934 can have a "button hook" shape, as shown in FIG. 29, with the bend between the first segment 2931 and the second segment 2933 having a value of about 180°. In other embodiments, the percutaneous probe 2934 can have other shapes. In any of those embodiments, part of the first segment 2931 can be spaced apart from part of the second segment 2933 by a separation distance SD. As described in greater detail below, the separation distance SD can be selected to provide a releasable yet secure, electrical connection with the coupling member 2961.

The coupling member 2961 can be carried by an actuator tool 2960 that releasably engages the actuator 2936 in a manner generally similar to that described above with reference to FIGS. 7-9. In one aspect of the embodiment, the coupling member 2961 can include an aperture 2963 having an aperture wall 2965, at least a portion of which is electrically conductive. The aperture wall 2965 can be electrically coupled to a conductor 2968 which provides electrical communication between the percutaneous probe 2934 and other devices, such as the controller 10 (FIG. 1E). In one aspect of the embodiment, the aperture 2963 has a diameter D which is at least slightly smaller than the separation distance SD. Accordingly, when the actuator tool 2960 is moved axially along a motion axis 2935, the first segment 2931 and the second segment 2933 of the percutaneous probe 2934 are received in the aperture 2963, with the first and second segments 2931 and 2933 forced into contact with the aperture wall 2965.

Figure 30:
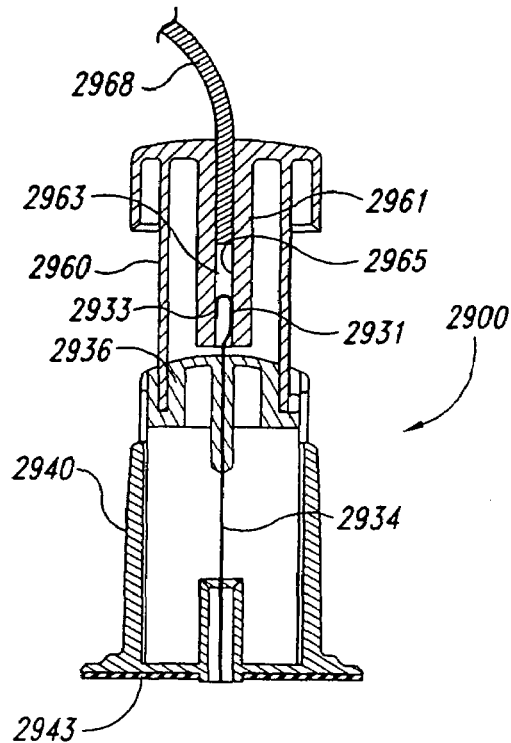
FIG. 30 is a partially schematic illustration of the apparatus shown in FIG. 29 with the coupling member electrically coupled to the percutaneous probe.

FIG. 30 illustrates the apparatus 2900 with the percutaneous probe 2934 received in the aperture 2963 of the coupling member 2961. As the percutaneous probe 2934 enters the aperture 2963, the first segment 2931 and the second segment 2933 can be forced slightly toward each and can exert an outwardly directed force against the aperture wall 2965. Accordingly, the aperture wall 2965 can form a secure, electrically conductive link between the conductor 2968 and the percutaneous probe 2934.

Once the percutaneous probe 2934 has been moved axially into the aperture 2963 of the coupling member 2961, the operator can rotate the actuator tool 2960 to engage it with the actuator 2936, and then move the actuator tool 2960 and the actuator 2936 together along the motion axis 2935 to deploy the percutaneous probe 2934, in a manner generally similar to that described above with reference to FIGS. 8 and 9. As the actuator tool 2960 rotates relative to the housing 2940, the first and second segments 2931, 2933 of the percutaneous probe 2934 can rub against the aperture wall 2965. One feature of the arrangement is that the rotational rubbing action can scrape away oxides or other contaminants that may build up on the percutaneous probe 2934 and/or the aperture wall 2965. An advantage of that feature is that reducing and/or eliminating oxides and/or other contaminants can increase the likelihood that a robust electrical connection is formed between the coupling member 2961 and the percutaneous probe 2934.

Another feature of the foregoing arrangement described above with reference to FIGS. 29 and 30 is that the first segment 2931 and the second segment 2933 can be resiliently biased toward a neutral configuration in which they are separated by the separation distance SD. As the percutaneous probe 2934 is received in the aperture 2963 of the coupling member 2961, the resilience of the percutaneous probe 2934 can tend to force at least one of the first segment 2931 and the second segment 2933 outwardly into engagement with the aperture wall 2965. As described above, an advantage of that feature is that it can provide a secure electrical connection between the coupling member 2961 and the percutaneous probe 2934.

Figure 31A:
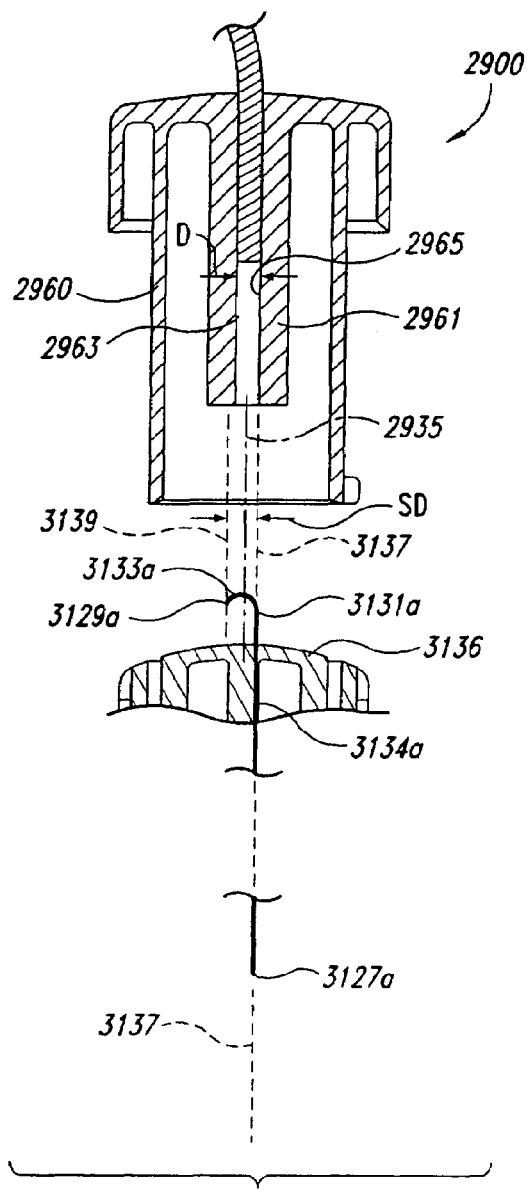
FIGS. 31A-34 are partially schematic, cross-sectional illustrations of apparatuses having percutaneous probes configured in accordance with further embodiments of the invention.

In other embodiments, the apparatus 2900 can have other coupling arrangements, such as those described below with reference to FIGS. 31A-35. Referring first to FIG. 31A, another embodiment of the apparatus 2900 can include a percutaneous probe 3134a carried by an actuator 3136 that is releasably coupleable to the actuator tool 2960. The percutaneous probe 3134a can include a first segment 3131a having a first end 3127a and a second segment 3133a having a second end 3129a. In one aspect of the embodiment, the percutaneous probe 3134a does not have a "button hook" shape. Instead, the first segment 3131a can be aligned with the first end 3127a along a first axis 3137 and the second end 3129a can be positioned on a second axis 3139 that is offset from the first axis 3137. As the actuator tool 2960 moves along the motion axis 2935, the second end 3129a and part of the first segment 3131a come into electrical contact with the aperture wall 2965 of the coupling member 2961. In a further aspect of the embodiment, the first axis 3137 and the second axis 3139 can be spaced apart by a separation distance SD which is slightly greater than the diameter D of the aperture 2963. Accordingly, the second end 3129a and the first segment 3131a can be resiliently forced into electrically conductive contact with the aperture wall 2965.

Figure 31B:
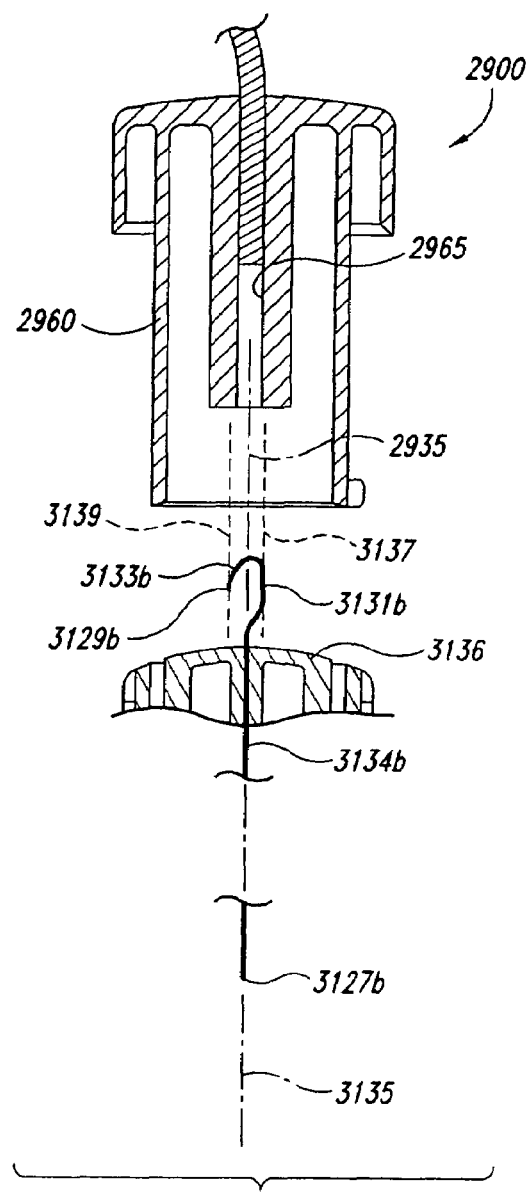

FIG. 31B is a partially schematic, cross-sectional illustration of the apparatus 2900 having a percutaneous probe 3134b configured in accordance with another embodiment of the invention. In one aspect of the embodiment, the percutaneous probe 3134b has a "button hook" shape with a first end 3127b of the percutaneous probe 3134b aligned along the motion axis 2935. The percutaneous probe 3134b can further include a first segment 3131b (at least part of which is aligned on the first axis 3137), and a second segment 3133b having a second end 3129b which is aligned on the second axis 3139. At least part of the first segment 3131b and the second end 3129b can be resiliently forced into engagement with the aperture wall 2965, in a manner generally similar to that described above with reference to FIG. 31A.

Figure 31C:
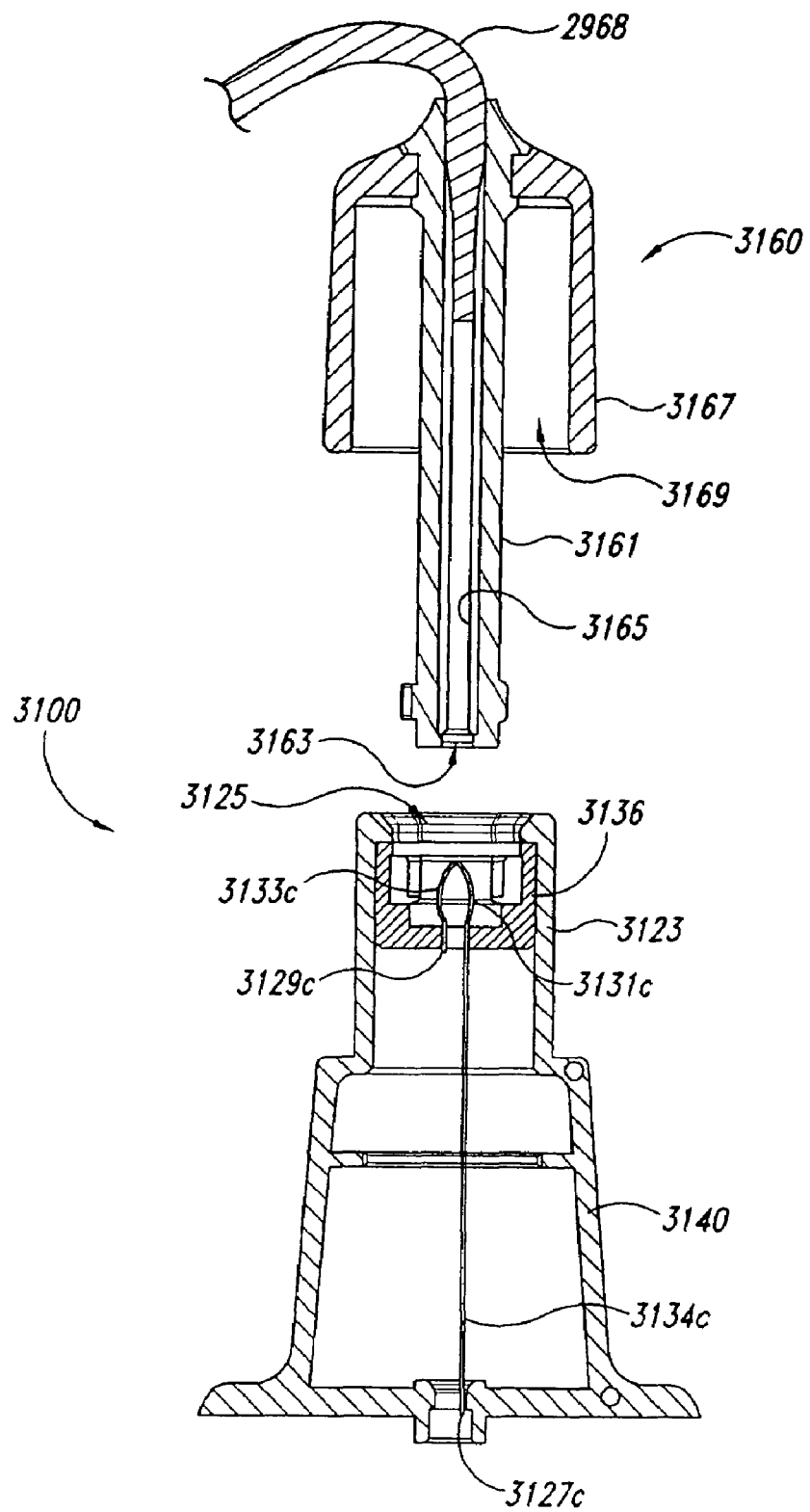

FIG. 31C is a partially schematic, cross-sectional illustration of an apparatus 3100 having a housing 3140 and an actuator tool 3160 configured in accordance with another embodiment of the invention. In one aspect of the embodiment, the housing 3140 includes an actuator 3136 that carries a percutaneous probe 3134c. The percutaneous probe 3134c can have a first, sharpened end 3127c, a second end 3129c, a first segment 3131c and a second segment 3133c. In one aspect of the embodiment, at least a portion of the first segment 3131c can face toward a portion of the second segment 3133c in a manner generally similar to that described above. Accordingly, the percutaneous probe 3134c can be securely, releasably, electrically coupled to the conductor 2968 carried by the actuator tool 3160, which can be removably inserted into a tool aperture 3125 of the housing 3140.

In a further aspect of the embodiment, the actuator tool 3160 can include a tool outer surface 3167 disposed annularly about a coupling member 3161, with a housing aperture 3169 between the outer surface 3167 and the coupling member 3161. The coupling member 3161 can include an aperture 3163 having a conductive surface 3165 that makes electrical contact with the percutaneous probe 3134c as the coupling member 3161 is inserted into the tool aperture 3125 of the housing 3140. As the actuator tool 3160 drives the actuator 3136 downwardly to deploy the percutaneous probe 3134c, an upper portion 3123 of the housing 3140 is received in the housing aperture 3169.

One feature of an arrangement described above with reference to FIG. 31C is that the uppermost portion of the percutaneous probe 3134c is recessed within the tool aperture 3125. An advantage of that arrangement is that the percutaneous probe 3134c is less exposed and accordingly is less likely to be damaged by incidental contact prior to engaging the actuator tool 3160 with the actuator 3136. Another feature of an embodiment of the arrangement described above with reference to FIG. 31C is that the tool 3160 can include a housing aperture 3169 that receives at least a portion of the housing 3140 when the tool 3160 deploys the percutaneous probe 3134c. An advantage of that arrangement is that the overall height of the housing 3140 and the tool 3160 when the percutaneous probe 3134c is deployed can be reduced, lessening the likelihood that the tool 3160 will be inadvertently jarred or knocked loose from the housing 3140, or that the housing 3140 will be knocked loose from the recipient.

Figure 32:
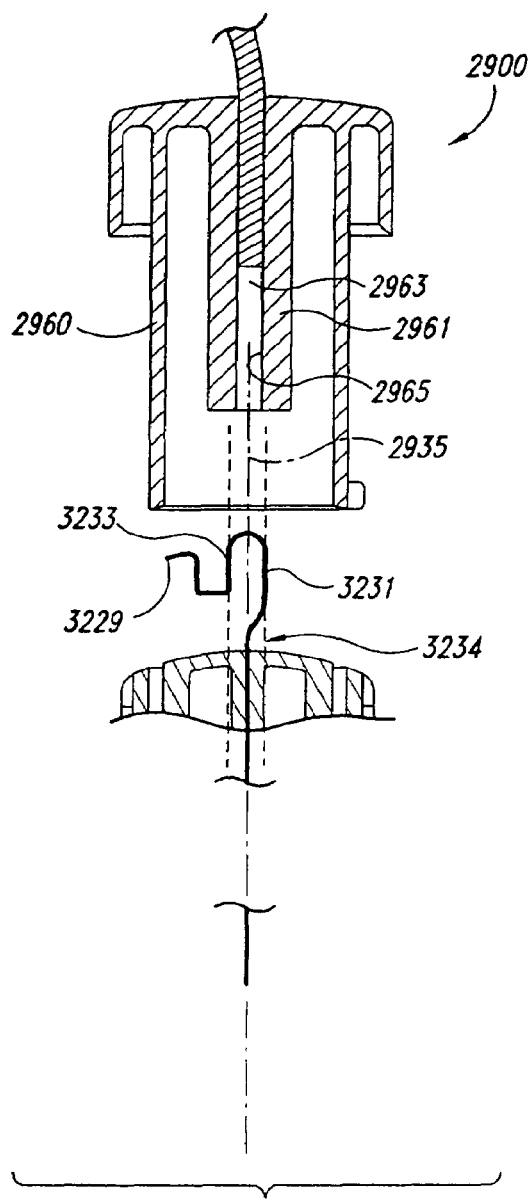

FIG. 32 is a partially schematic, cross-sectional illustration of an apparatus 2900 having a probe 3234 with a second end 3229 that is not received in the aperture 2963 of the coupling member 2961. In one aspect of the embodiment, the percutaneous probe 3234 can include a first segment 3231 and a second segment 3233, at least portions of which face toward each other. The facing portions of the first segment 3231 and the second segment 3233 can be received in the aperture 2963 while the second end 3229 remains external to the aperture 2963. The first segment 3231 and the second segment 3233 can be resiliently biased toward a neutral position (shown in FIG. 32) so as to be forced into engagement with the aperture wall 2965 when the coupling member 2961 is moved axially along the motion axis 2935 to receive the percutaneous probe 3234.

Figure 33:
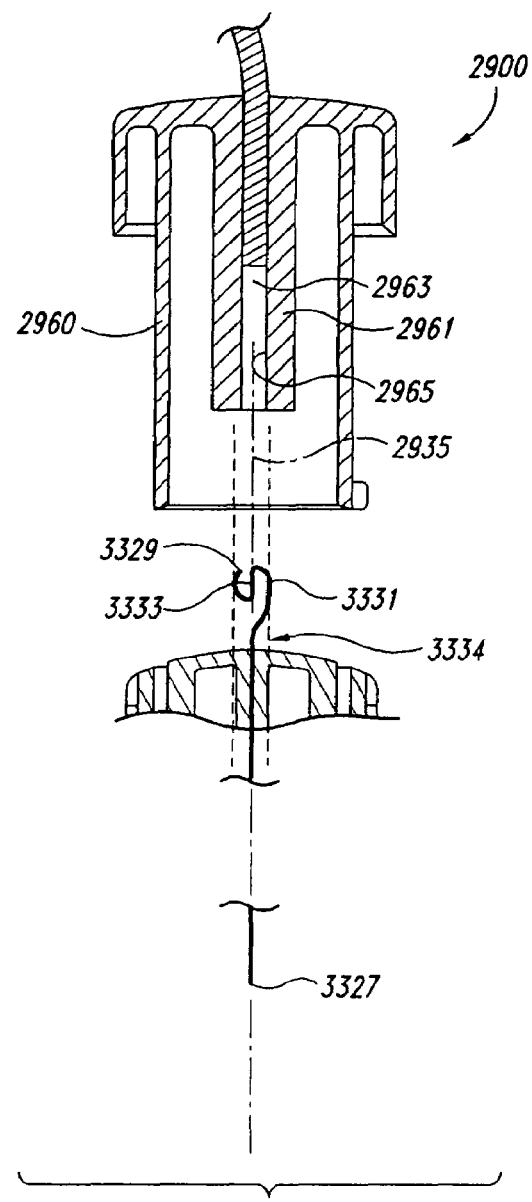

FIG. 33 is a partially schematic, cross-sectional illustration of an embodiment of the apparatus 2900 which includes a percutaneous probe 3334 having a second end 3329 that faces opposite from a first end 3327 and is received in the aperture 2963 of the coupling member 2961. In one aspect of the embodiment, the percutaneous probe 3334 includes a first segment 3331 and a second segment 3333 which doubles back on itself as shown in FIG. 33. Portions of the first segment 3331 and the second segment 3333 can accordingly be forced against the aperture wall 2965 as they are received in the aperture 2963, in a manner generally similar to that described above with reference to FIGS. 29-32. In one aspect of the embodiment, the doubled back second segment 3333 can provide a greater contact force between the percutaneous probe 3334 and the aperture wall 2965. Such an arrangement can be suitable for particular percutaneous probes 3334, including percutaneous probes 3334 having very small diameters. For such percutaneous probes 3334, a single bend between the first segment 3331 and the second segment 3333 may not provide sufficient biasing force to provide for a secure electrical connection.

Figure 34:
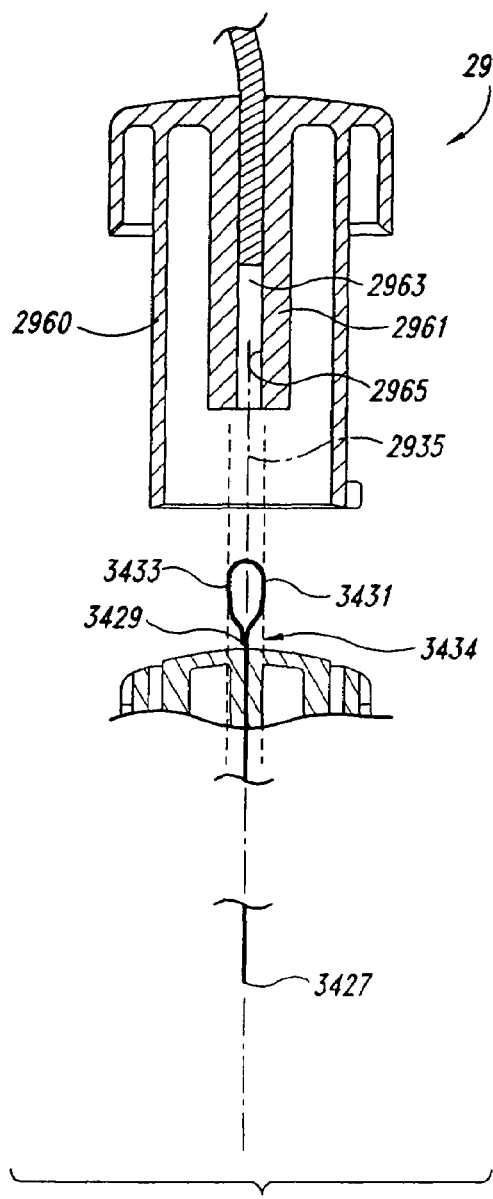

FIG. 34 is a partially schematic, cross-sectional illustration of an embodiment of the apparatus 2900 having a percutaneous probe 3434 with a first segment 3431 having a first end 3427, and a second segment 3433 having a second end 3429 that doubles back to contact the first segment 3431. In one aspect of the embodiment, the second end 3429 can loosely contact the first segment 3431 and can be urged against the first segment 3431 when the percutaneous probe 3434 is received in the aperture 2963 of the coupling member 2961. In another embodiment, the second end 3429 can be urged past the first segment 3431 (e.g., to the right as shown in FIG. 34) when the percutaneous probe 3434 is received in the aperture 2963. In yet another embodiment, the second end 3429 can be connected to the first segment 3431 (e.g., by soldering, brazing, welding, or other conventional attachment methods) to form a fixed joint. One result of attaching the second end 3429 to the first segment 3431 is that the arrangement can increase the force required to displace at least one of the first segment 3431 and the second segment 3433 relative to the other. An advantage of that feature is that it can provide for a greater contact force between the percutaneous probe 3434 and the aperture wall 2965, and can accordingly provide a more secure electrical connection between the percutaneous probe 3434 and the coupling member 2961. Another advantage of the arrangement is that the second end 3429 can be less likely to catch or snag on the aperture wall 2965 as the percutaneous probe 3434 is deployed and/or retracted, which can improve the reliability and operability of the apparatus 2900.

Figure 35:
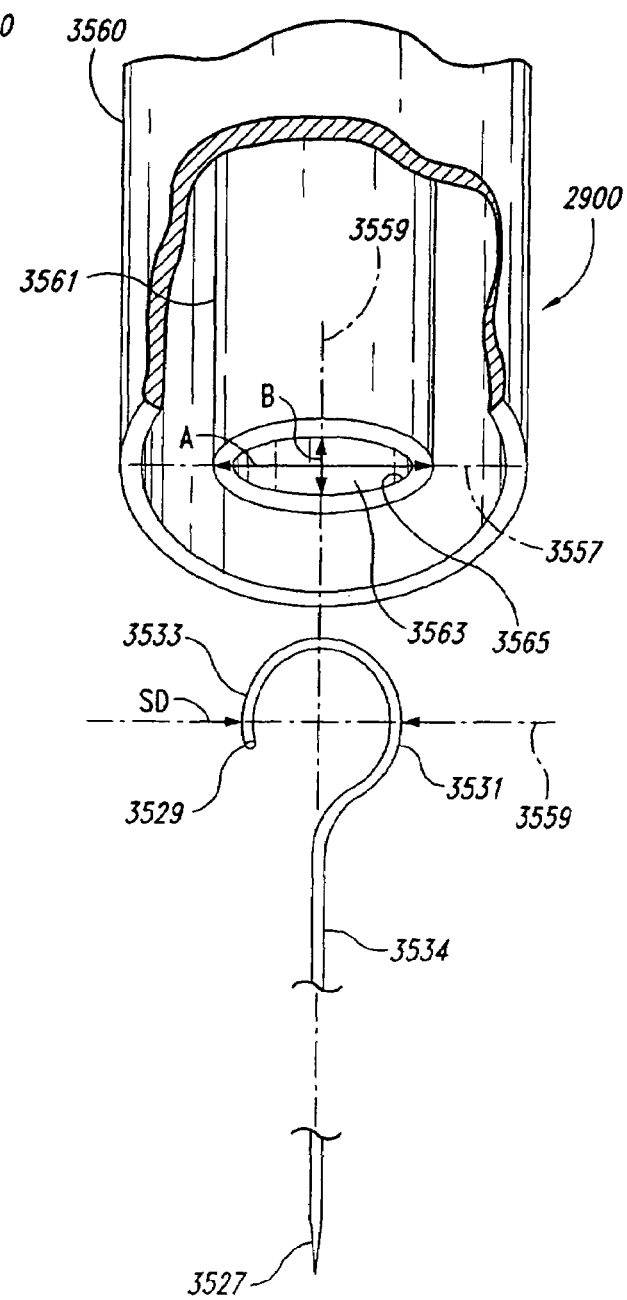
FIG. 35 is a partially schematic, isometric illustration of a portion of an apparatus having a non-concentric coupling member in accordance with still a further embodiment of the invention.

FIG. 35 is a partially schematic, partially cut-away isometric illustration of an apparatus 2900 having an actuator tool 3560 with a non-axisymmetric coupling member 3561 that receives a percutaneous probe 3534 in accordance with another embodiment of the invention. In one aspect of the embodiment, the coupling member 3561 can include an aperture 3563 having a non-circular cross-sectional shape and a conductive aperture wall 3565. For example, the aperture 3563 can have an elliptical cross-sectional shape. In one aspect of the embodiment, the aperture 3563 can have a major dimension A along a major axis 3557, and a minor dimension B along a minor axis 3559. The percutaneous probe 3534 can include a first segment 3531 having a sharp first end 3527 and a second segment 3533 having a second end 3529. A portion of the first segment 3531 can be spaced apart from a corresponding portion of the second segment 3533 by separation distance SD (measured along a transverse axis 3559) that is less than the major dimension A. Accordingly, the percutaneous probe 3534 and the coupling member 3561 can be positioned with the transverse axis 3559 of the percutaneous probe 3534 aligned with the major axis 3557 of the coupling member 3561. As the coupling member 3561 is moved along the motion axis 2935 toward the percutaneous probe 3534, the first segment 3531 and the second segment 3533 can be received in the aperture 3563 without the percutaneous probe 3534 contacting the aperture wall 3565. When the operator then rotates the actuator tool 3560 relative to the percutaneous probe 3534 (as described above with reference to FIGS. 29 and 30), the first segment 3531 and the second segment 3533 can come into contact with the aperture wall 2965 to provide a secure, releasable electrical connection between the percutaneous probe 3534 and the coupling member 3561.

One feature of an embodiment of the apparatus 2900 described above with reference to FIG. 35 is that the percutaneous probe 3534 can be axially received in the aperture 3563 of the coupling member 3561 without engaging the surfaces of the percutaneous probe 3534 with the aperture wall 3565. An advantage of that feature is that the percutaneous probe 3534 can be received in the aperture 3563 without imparting an axial force to the percutaneous probe 3534 (e.g., a "zero insertion force" arrangement). Accordingly, the process of receiving the percutaneous probe 3534 in the aperture 3563 can be more comfortable for the recipient.

Another feature of an embodiment of the foregoing arrangement is that the force required to provide electrical contact between the percutaneous probe 3534 and the coupling member 3561 can be purely rotational. An advantage of that feature is that the operator need not apply an axial force to the percutaneous probe 3534 or the housing 2940 (FIG. 29) when electrically engaging the percutaneous probe 3534 with the coupling member 3561, which can further increase the recipient's comfort.

A further advantage of an embodiment of the foregoing arrangement is that the force required to provide secure electrical contact between the percutaneous probe 3534 and the coupling member 3561 can be increased without increasing the axial force applied to the recipient. For example, portions of the percutaneous probe 3534 (or the entire percutaneous probe 3534) can be made of a heavier gauge material, which can require the operator to apply an increased rotational force to engage the percutaneous probe 3534 with the coupling number 3561, without requiring the operator to apply an increased axial force. In another arrangement, the force required to engage the percutaneous probe 3534 with the coupling member 3561 can be increased by connecting the second end 3529 to the first segment 3531 (in a manner generally similar to that described above with reference to FIG. 34), or by configuring the second segment 3533 to double back (in a manner generally similar to that described above with reference to FIG. 33). In any of those embodiments, the increased force required to engage the percutaneous probe 3534 with the coupling member 3561 can improve the security of the electrical contact between these two components without increasing the axial force applied to the recipient.

Figure 36A:
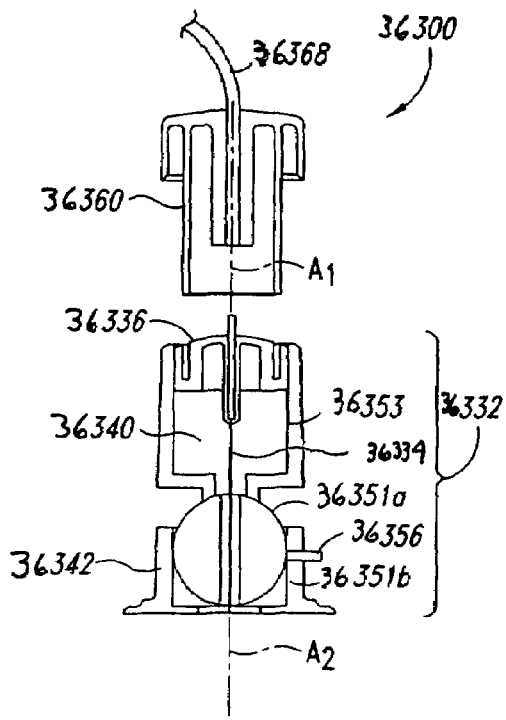
FIG. 36A is a partially schematic, cross-sectional illustration of an apparatus configured to deploy a percutaneous probe in accordance with one embodiment of the invention.

FIG. 36A is a partially schematic, cross-sectional illustration of an apparatus 36300 configured to deploy a percutaneous probe 36334 in accordance with one embodiment of the invention. In one aspect of the embodiment, the percutaneous probe 36334 can include a percutaneous electrode, and in other embodiments, the percutaneous probe 36334 can include a diagnostic electrode, an acupuncture needle, a drug delivery needle, a liquid extraction needle, or another sharp-ended percutaneous device.

The apparatus 36300 includes a housing 36332 in which the percutaneous probe 36334 is movably disposed. The housing 36332 can include a first portion 36340 and a second portion 36342 movably coupled to the first portion 36340 to orient the percutaneous probe 36334 at a selected angle. For example, in the embodiment illustrated in FIG. 36A, the first portion 36340 is coupled to the second portion 36342 by a ball and socket connection 36351. More specifically, the first portion 36340 includes a ball 36351a and the second portion 36342 includes a socket 36351b in which the ball 36351a is received for rotational movement. Accordingly, the first portion 36340 of the housing 36332 can move relative to the second portion 36342 to orient the percutaneous probe 36334 at a selected angle. In additional embodiments, the first portion 36340 can include the socket 36351b and the second portion 36342 can include the ball 36351a. In other embodiments, including those described below with reference to FIGS. 37A-39C, the first portion 36340 can be movably coupled to the second portion 36342 by other devices.

In the embodiment illustrated in FIG. 36A, the first portion 36340 can include a first longitudinal axis $A_1$, and the second portion can include a second longitudinal axis $A_2$ that can be initially generally parallel to and coaxial with the first longitudinal axis $A_1$. As described in greater detail below, the first portion 36340 or the second portion 36342 can move so that the first longitudinal axis $A_1$ is then transverse or inclined relative to the second longitudinal axis $A_2$.

The housing 36332 can also include a locking device 36356 to selectively prevent the first portion 36340 from moving relative to the second portion 36342, for example when the probe 36334 is oriented at a selected angle for insertion into the recipient. In the illustrated embodiment, for example, the locking device 36356 can include a set screw that selectively exerts a force on the ball 36351a to restrict movement of the ball 36351a within the socket 36351b. In additional embodiments, the ball can be selectively expandable or the locking device 36356 can include other devices, such as pins or detents.

In a further aspect of the embodiment, the apparatus 36300 includes an actuator 36336 that carries the percutaneous probe 36334. The actuator 36336 can removably receive an actuator tool 36360. Accordingly, an operator can move the percutaneous probe 36334 from a stowed position (shown in FIG. 36A) to one or more deployed positions (described below with reference to FIG. 36C).

Figure 36B:
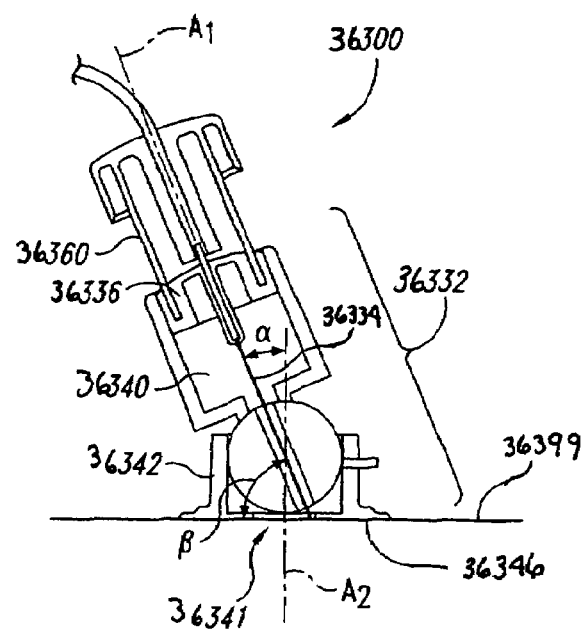
FIG. 36B is a partially schematic, cross-sectional illustration of the apparatus of FIG. 36A positioned against a recipient's skin with the percutaneous probe oriented at a selected angle with respect to the skin.

FIG. 36B illustrates the apparatus 36300 of FIG. 36A positioned against a recipient's skin 36399 with the percutaneous probe 36334 oriented at a selected angle with respect to the skin 36399. The second portion 36342 of the housing 36332 includes a lower surface 36346 configured to be positioned against or at least proximate to the recipient's skin 36399. The lower surface 36346 has an aperture 36341 sized to permit the percutaneous probe 36334 to pass out of the housing 36332 during deployment at any one of a plurality of angles. The lower surface 36346 can be mounted to a selected site on the recipient's skin 36399 with an adhesive (not shown). The adhesive can be applied to the recipient's skin 36399 or the lower surface 36346 to adhere the apparatus 36300 to the recipient's skin 36399. In other embodiments, the second portion 36342 of the housing 36332 can be attached to the recipient with other devices.

As shown in FIG. 36B, the first portion 36340 of the housing 36332 has been moved relative to the second portion 36342 to orient the percutaneous probe 36334 for insertion into the recipient at a selected angle $\beta$. The first portion 36340 can be moved before or after the apparatus 36300 is mounted to the recipient. In the illustrated embodiment, the first axis $A_1$ and the second axis $A_2$ are transverse and intersect to form an angle $\alpha$. Accordingly, the first axis A₁ and the percutaneous probe 36334 are oriented at the selected angle β with respect to the recipient's skin 36399 and a plane defined by the lower surface 36346.

Figure 36C:
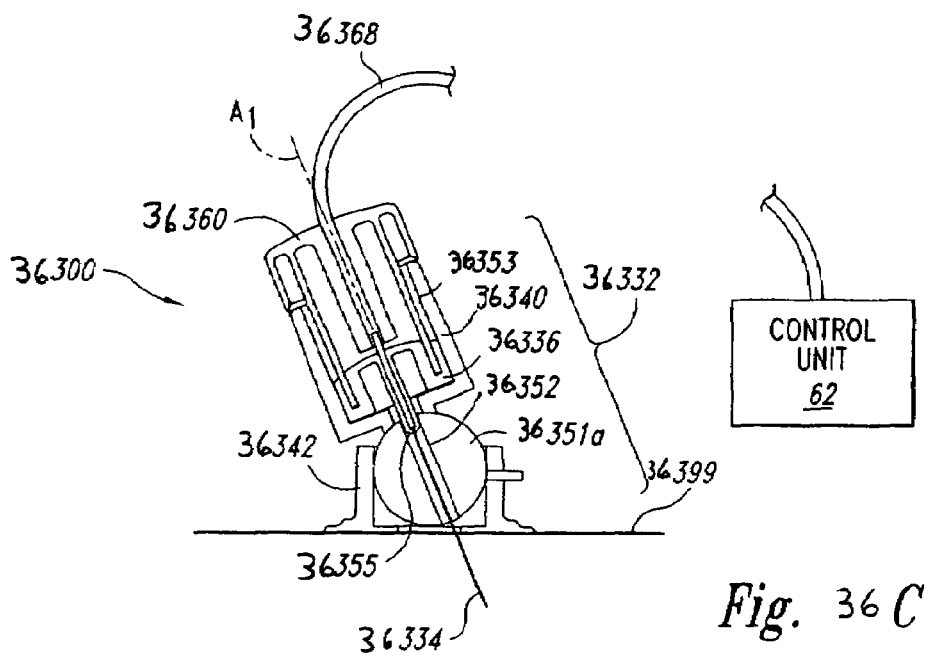
FIG. 36C is a partially schematic, cross-sectional illustration of the apparatus of FIG. 36B with the percutaneous probe inserted into the recipient.
Figure 37:
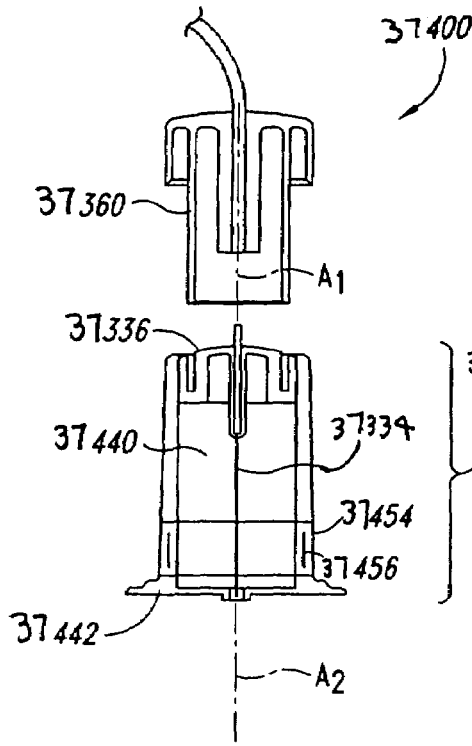
FIG. 37A is a partially schematic, cross-sectional illustration of an apparatus configured to deploy a percutaneous probe in accordance with another embodiment of the invention.
FIG. 37B is a partially schematic, cross-sectional illustration of the apparatus of FIG. 37A positioned against the recipient's skin with the percutaneous probe oriented at a selected angle with respect to the skin.
FIG. 37C is a partially schematic, cross-sectional illustration of the apparatus of FIG. 37B with the percutaneous probe inserted into the recipient.
Figure 37:
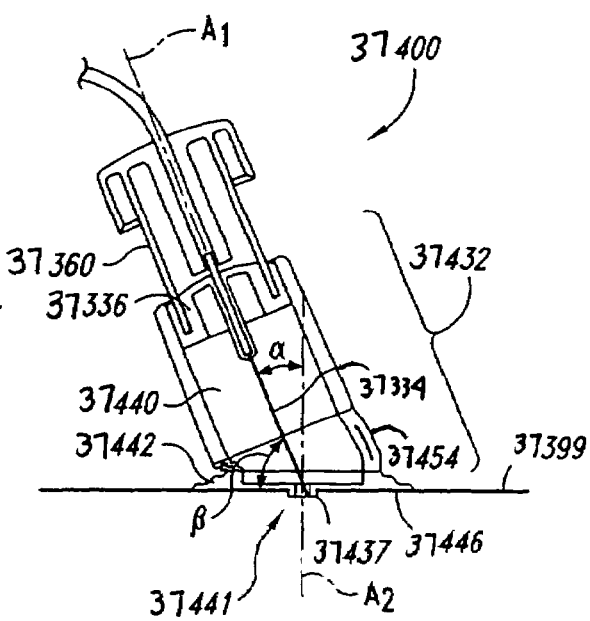
Figure 37:
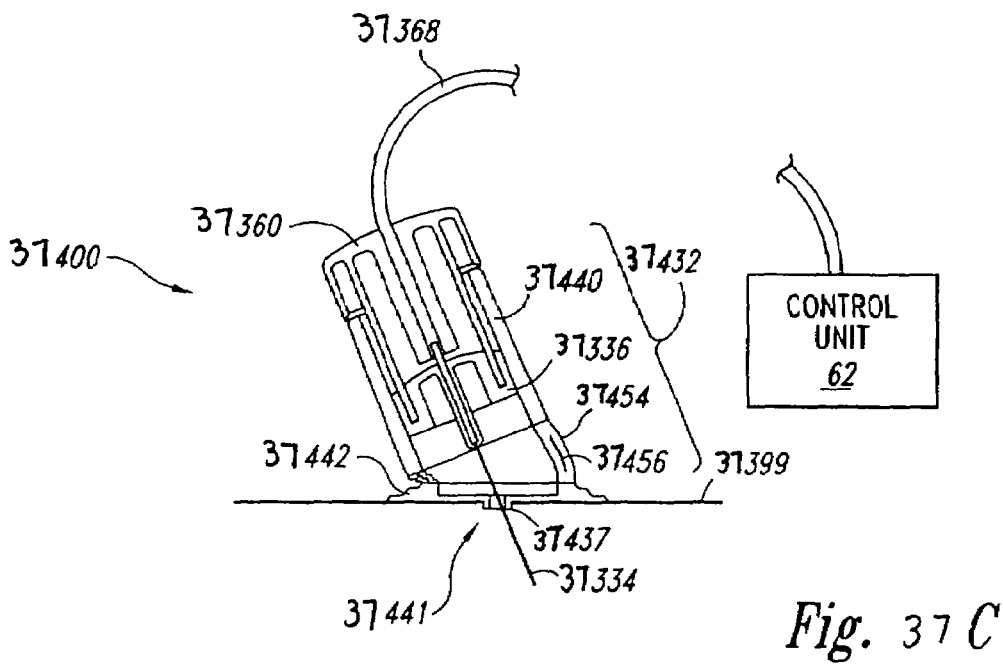

FIG. 36C illustrates the apparatus 36300 of FIG. 36B with the percutaneous probe 36334 inserted into the recipient. The percutaneous probe 36334 is deployed by driving the actuator tool 36360 along the first axis A₁ toward the recipient. Consequently, the actuator 36336 moves through a chamber 36353 of the first portion 36340, driving the percutaneous probe 36334 along the first axis A₁ and through the recipient's skin 36399. A channel 36352 in the ball 36351a can provide axial support to the percutaneous probe 36334 and a projection 36355 of the actuator 36336 during insertion.

In one embodiment, for example, when the percutaneous probe 36334 includes an electrode configured to transmit and/or receive electrical signals, the actuator tool 36360 can also include a conductor 36368 which is coupleable to the control unit 62. In another embodiment, for example, when the percutaneous probe 36334 includes a hollow needle for delivering substances, such as liquid drugs, or extracting bodily liquids, the conductor 36368 can be replaced with a flexible fluid delivery conduit.

One feature of the apparatus illustrated in FIGS. 36A-C is that the percutaneous probe can be inserted into a recipient at any one of a variety of angles while remaining stably positioned against the recipient's skin. An advantage of this feature is that a practitioner or other operator may position the percutaneous probe at the most comfortable, convenient, and/or effective orientation and/or location on the recipient to deliver treatment in an optimal fashion. Furthermore, the housing can be positioned at one location on the recipient's skin and treatment can be applied to locations in addition to the location directly beneath the housing.

FIG. 37A is a partially schematic, cross-sectional illustration of an apparatus 37400 configured to deploy a percutaneous probe 37334 in accordance with another embodiment of the invention. The apparatus 37400 is generally similar to the apparatus 37300 described above with reference to FIGS. 36A-C. For example, the apparatus 37400 includes an actuator 37336 to carry the percutaneous probe 37334, an actuator tool 37360 configured to drive the actuator 37336, and a housing 37432. The housing 37432 includes a first portion 37440 having a first axis A₁, a second portion 37442 having a second axis A₂, and a flexible portion 37454 coupled to the first and second portions 37440 and 37442. The flexible portion 37454 flexes and/or deforms to allow the first portion 37440 to move relative to the second portion 37442 to orient the percutaneous probe 37334 at a selected angle. In one embodiment, the flexible portion 37454 can include a thermoplastic, elastomeric material. In other embodiments, other deformable materials can be used.

The flexible portion 37454 of the housing 37432 can include a locking device 37456 to selectively prevent the first portion 37440 from moving relative to the second portion 37442, and accordingly, maintain the selected orientation of the percutaneous probe 37334. In one embodiment, for example, the locking device 37456 can include a plurality of elements embedded within the flexible portion 37454. The elements can be strips of a material having memory, including wires or metallic strips. Accordingly, when the first portion 37440 is moved relative to the second portion 37442 and the flexible portion 37454 is deformed, the locking device 37456 retains the flexible portion 37454 in its deformed shape and thus maintains the selected orientation of the percutaneous probe 37334. In other embodiments, other locking devices can be used.

FIG. 37B illustrates the apparatus 37400 of FIG. 37A positioned against the recipient's skin 37399 with the percutaneous probe 37334 oriented at a selected angle with respect to the skin 37399. The first portion 37440 of the housing 37432 has been moved relative to the second portion 37442 to orient the percutaneous probe 37334 for insertion into the recipient at a selected angle β. Accordingly, the first axis A₁ intersects the second axis A₂ to form an angle α. In the illustrated embodiment, the second portion 37442 of the housing 37432 includes a lower surface 37446 configured to be positioned against or at least proximate to the recipient's skin 37399. The lower surface 37446 has a projection 37437 with an aperture 37441 sized to permit the percutaneous probe 37334 to pass out of the housing 37432 during deployment. The projection 37437 can stretch the recipient's skin 37399 proximate to the point at which the percutaneous probe 37334 pierces the skin 37399 and can accordingly reduce the magnitude of the sensation felt by the recipient when the percutaneous probe 37334 is deployed. In other embodiments, the lower surface 446 may not include the projection 37437.

FIG. 37C illustrates the apparatus 37400 of FIG. 37B with the percutaneous probe 37334 inserted into the recipient. The actuator tool 37360 drives the actuator 37336 to deploy the percutaneous probe 37334 in a manner generally similar to that described above with reference to FIGS. 36A-C. The locking device 37456 can restrict movement between the first portion 37440 and the second portion 37442 and thus maintain the selected orientation of the probe 37334 during insertion. The projection 37437 and the aperture 37441 can be sized to provide axial support to the percutaneous probe 37334 during deployment. In additional embodiments, the apparatus 37400 may also include a probe guide, similar to the channel 42 discussed above with reference to FIGS. 4-9. The probe guide can be coupled to the first or second portion 37440 or 37442 to provide axial support to the percutaneous probe 37334.

FIG. 38A is a partially schematic, cross-sectional illustration of an apparatus 38500 configured to deploy a percutaneous probe 38334 in accordance with another embodiment of the invention. The apparatus 38500 includes an actuator 38336 configured to carry the percutaneous probe 38334, an actuator tool 38360 configured to drive the actuator 38336, and a housing 38532. The housing 38532 includes a first portion 38540 having a first axis A₁ and a second portion 38542 having a second axis A₂. The first portion 38540 is pivotably coupled to the second portion 38542 by a hinge 38554. The hinge 38554 permits the first portion 38540 to move in a direction P relative to the second portion 38542 to orient the percutaneous probe 38334 at a selected angle.

FIG. 38B illustrates the apparatus 38500 of FIG. 38A positioned against the recipient's skin 38399 with the percutaneous probe 38334 oriented at a selected angle with respect to the skin 38399. The first portion 38540 of the housing 38532 has been rotated in the direction P to orient the percutaneous probe 38334 at a selected angle β with respect to the recipient's skin 38399. The rotation of the first portion 38540 creates a gap G in the housing 38532 between the first and second portions 38540 and 38542. The second portion 38542 of the housing 38532 has a lower surface 38546 configured to be positioned against or at least proximate to the recipient's skin 38399. The lower surface 38546 has an aperture 38541 sized to permit the percutaneous probe 38334 to pass out of the housing 38532 during deployment.

FIG. 38C illustrates the apparatus 38500 of FIG. 38B with the percutaneous probe 38334 inserted into the recipient. In other embodiments the apparatus 38500 can include a locking device to prevent the first portion 38540 from moving relative to the second portion 38542 during insertion of the percutaneous probe 38334 into the recipient. For example, the locking device can include a releasable clamp at the hinge 38554 that can be selectively engaged to prevent movement of the first portion 38540 relative to the second portion 38542.

Figures 39A, 39B:
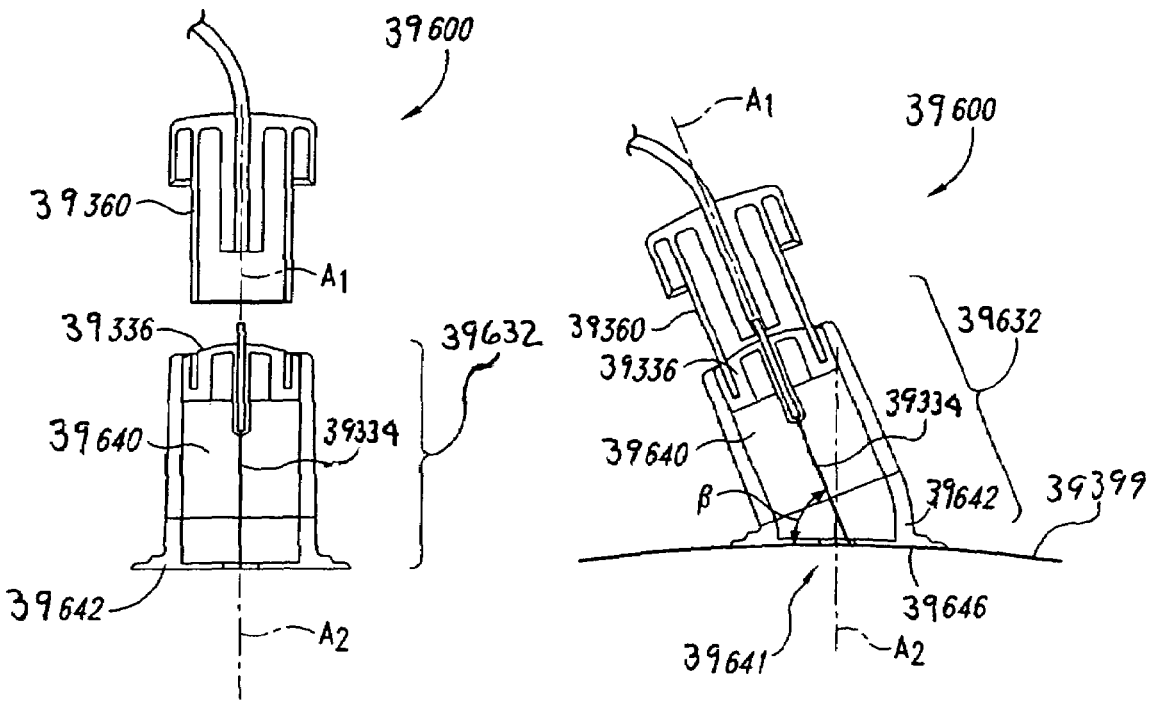
FIG. 39A is a partially schematic, cross-sectional illustration of an apparatus configured to deploy a percutaneous probe in accordance with another embodiment of the invention.
FIG. 39B is a partially schematic, cross-sectional illustration of the apparatus of FIG. 39A positioned against the recipient's skin with the percutaneous probe oriented at a selected angle.

FIG. 39A is a partially schematic, cross-sectional illustration of an apparatus 39600 configured to deploy a percutaneous probe 39334 in accordance with another embodiment of the invention. The apparatus 39600 includes an actuator 39336 configured to carry the percutaneous probe 39334, an actuator tool 39360 configured to drive the actuator 39336, and a housing 39632. The housing 39632 includes a first portion 39640 having a first axis $A_1$ and a second portion 39642 having a second axis $A_2$ coupled to the first portion 39640. The second portion 39642 is flexible in a manner generally similar to that described above with reference to the flexible portion 39454 shown in FIGS. 37A-C. Accordingly, the second portion 39642 flexes and/or deforms to allow the housing 39632 to orient the percutaneous probe 39334 at a selected angle.

FIG. 39B illustrates the apparatus 39600 of FIG. 39A positioned against the recipient's skin 39399 with the percutaneous probe 39334 oriented at the selected angle. The second portion 39642 has deformed in shape and has a lower surface 39646 positioned against the recipient's skin 39399. In this embodiment, the lower surface 39646 flexes to follow the contours of the recipient's skin 39399. The lower surface 39646 also has an aperture 39641 sized to permit the percutaneous probe 39334 to pass through the aperture 39641 during deployment. The lower surface 39646 can define a plane that is perpendicular to the second axis $A_2$. Accordingly, in the illustrated embodiment, the first axis $A_1$ and the percutaneous probe 39334 are transverse to the second axis $A_2$ and oriented at a selected angle β with respect to the recipient's skin 39399.

Figure 39C:
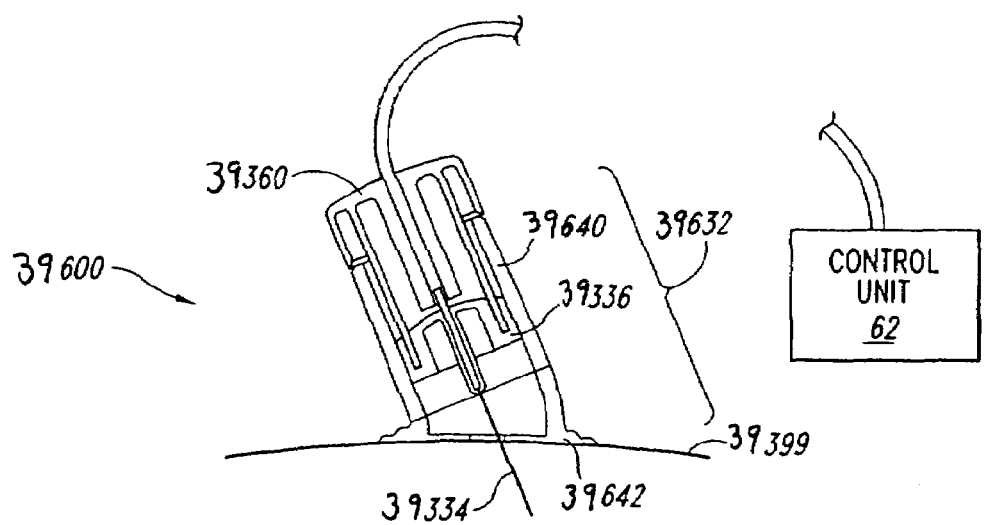
FIG. 39C is a partially schematic, cross-sectional illustration of the apparatus of FIG. 39B with the percutaneous probe inserted into the recipient.

FIG. 39C illustrates the apparatus 39600 of FIG. 39B with the percutaneous probe 39334 inserted into the recipient. In other embodiments, the second portion 39642 can also include a locking device, such as the locking device 39456 discussed above with reference to FIGS. 37A-C, to maintain the selected orientation of the percutaneous probe 39334 during deployment.

Figures 40A, 40B, 40C:
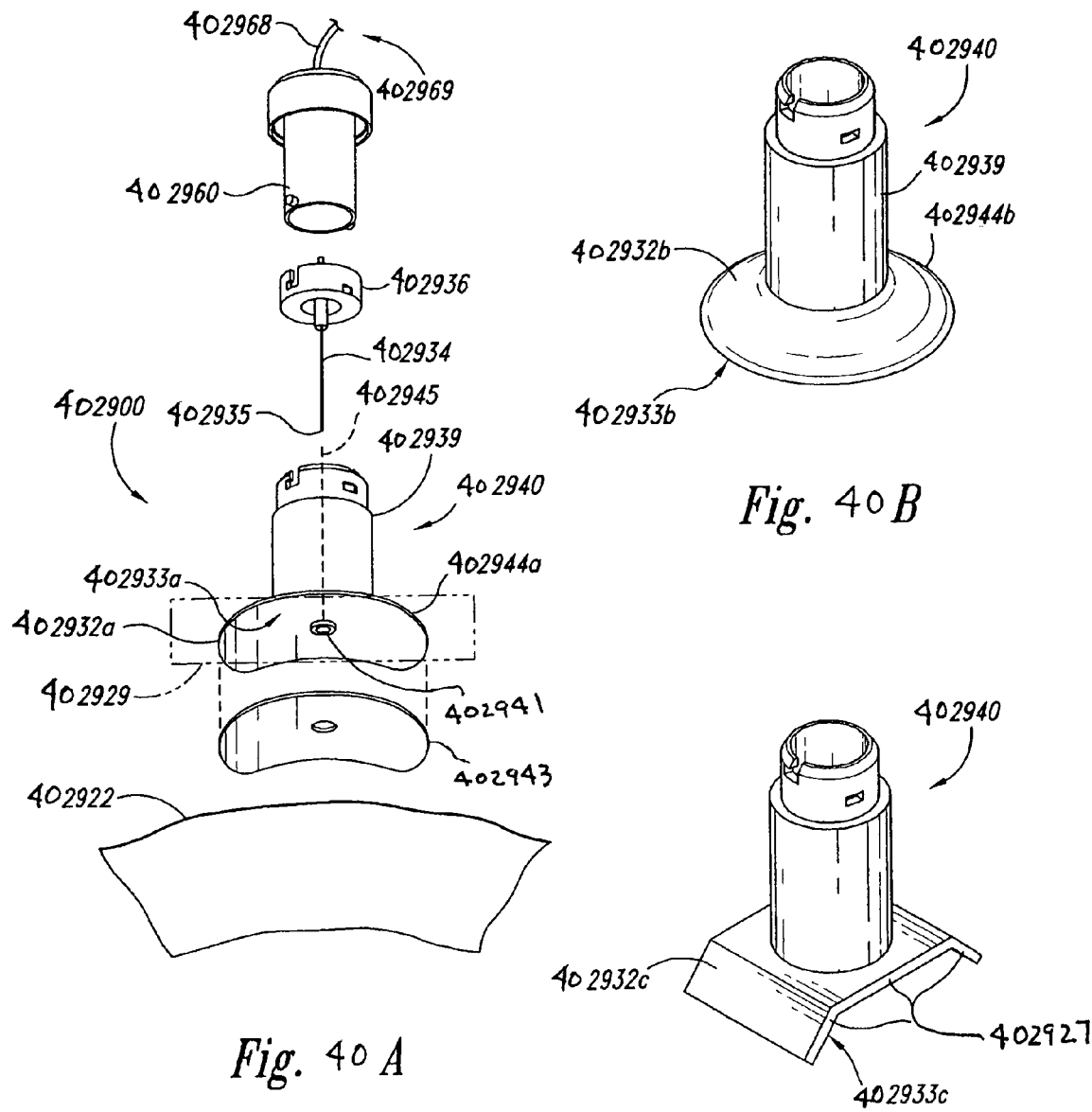
FIG. 40A is a partially exploded view of an apparatus having a percutaneous probe housing with a contoured base in accordance with the embodiment of the invention.
FIG. 40B is a partially schematic, isometric view of a percutaneous probe housing having a contoured support surface configured in accordance with another embodiment of the invention.
FIG. 40C is a partially schematic, isometric view of a percutaneous probe housing having a contoured support surface configured in accordance with still another embodiment of the invention.

FIG. 40A is a partially schematic, partially exploded isometric view of a percutaneous apparatus 402900 having a housing 402940 shaped in accordance with another embodiment of the invention. In one aspect of the embodiment, the housing 402940 includes a probe portion 402939 and a support member 402932a. The probe portion 402939 can have a generally cylindrical shape elongated along a probe axis 402945. The probe portion 402939 can carry an actuator 402936 which in turn carries a percutaneous probe 402934 for movement relative to the housing 402940 in a manner generally similar to that described above with reference to FIGS. 4-9. In one embodiment, the percutaneous probe 402934 can include a diagnostic and/or therapeutic electrode. Accordingly, the actuator 402936 carrying the percutaneous probe 402934 can be actuated by an actuator tool 402960 having a conductor 402968. The conductor 402968 can form a portion of a conductive link 402969 between the percutaneous probe 402934 and the control unit 10 (FIG. 1E). In other embodiments, the percutaneous probe 402934 can include other devices. For example, in one embodiment, the percutaneous probe 402934 can include an acupuncture needle and in other embodiments, the percutaneous probe 402934 can include a hollow needle suitable for drug delivery to and/or fluid extraction from the recipient. In any of those embodiments, the percutaneous probe 402934 can include a sharp end 402935 which is movable relative to the support member 402932a between a stowed position (with the sharp end 402935 located within the housing 402940) to a deployed position (with the sharp end 402935 located external to the housing 402940).

The support member 402932a can include a flange 402944a having an exit aperture 402941 through which the percutaneous probe 402934 moves as it is deployed. In one embodiment, the support member 402932a can have a contoured support surface 402933a, which is curved or otherwise shaped so as to include portions that are not parallel to a flat reference plane 402929 extending generally transversely to the probe axis 402945. In one aspect of the embodiment, the support surface 402933a can have an at least partially cylindrical shape, and in other embodiments, the support surface 402933a can have other shapes, such as those described below with reference to FIGS. 40B-40C. In any of those embodiments, the housing 402940 can further include an attachment device 402943 (shown spaced apart from the housing in FIG. 40A for purposes of illustration) that releasably connects the housing 402940 to a skin surface 402922 of the recipient. For example, the attachment device 402943 can include an adhesive layer or another adhesive element attached to the support surface 402933a and releasably attachable to the skin surface 402922. In other embodiments, the attachment device 402943 can have other configurations. In any of those embodiments, the support surface 402933a can face toward the skin surface 402922 when the housing 402940 is attached to the skin surface 402933a. Accordingly, the support surface 402922 can stabilize the housing 402940 relative to the skin surface 402922.

In other embodiments, the housing 402940 can include support members having other non-planar shapes. For example, referring now to FIG. 40B, the housing 402940 can include a support member 402932b having an at least partially spherical support surface 402933b. Accordingly, the support surface 402933b can form a portion of a flange 402944b extending outwardly from the upwardly projecting cylindrical probe portion 402939. In other embodiments, the support surface can have still further shapes. For example, the support surface can include a combination of cylindrical and spherical or otherwise curved surface portions. In one particular embodiment, shown in FIG. 40C, the housing 402940 can include a support member 402932c having a downwardly facing support surface 402933c that as a whole is contoured to have a non-flat shape, but that includes a plurality of flat surface portions 402927 inclined relative to each other. In one aspect of this embodiment, the support member 402932c can include three flat surface portions 402927, and in other embodiments, the support member 402932c can include more or fewer flat surface portions 402927.

One feature of embodiments of the apparatus 402900 described above with reference to FIGS. 40A-40C is that the support members can have contoured (e.g., non-planar, non-flat) shapes. An advantage of that feature is that the support surfaces can more closely match the corresponding non-planar skin surface of the recipient to which they are attached. The degree to which a particular support member departs from a flat shape can be selected to depend upon the region of the recipient's body to which the corresponding housing 402940 is attached. For example, the support member can be selected to have a relatively gentle rate of curvature when it is to be attached to a relatively flat body portion of the recipient, such as the lower back or lumbar region, or when the support member is to be attached to a recipient having a relatively large body size. The support member can be selected to have a higher degree of curvature when it is to be attached to a portion of the recipient having a relatively high degree of curvature, such as the cervical or neck region of the recipient, or when the corresponding housing 402940 is to be attached to a recipient having a relatively small body size. In any of those embodiments, the contoured support member can be more comfortable for the recipient than a planar support member. Embodiments of the support member can also be less likely to be inadvertently jarred loose from the recipient, because they can have a relatively large amount of surface area in contact with the recipient's skin surface 402922.

In other embodiments, the housing 402940 can have support members with other configurations. For example, referring now to FIG. 41, the housing 412940 can include a probe portion 412939 having an actuator 412936 carrying a percutaneous probe 412934, and can further include a flexible support member 413032. In one aspect of the embodiment, the flexible support member 413032 can deflect in at least two opposing directions (e.g., upwardly and downwardly) toward the probe axis 412945 from a neutral position (shown in solid lines in FIG. 41) to one or more displaced positions (two of which are shown in dashed lines in FIG. 41), as indicated by arrows A. In one embodiment, the support member 413032 can include a resilient, flexible material that tends to return to its neutral position. Suitable materials include Santoprene and other flexible, soft plastics. In another embodiment, the support member 413032 can include a material that retains its shape when deflected. For example the support member 413032 can include radially extending wire stays that allow the operator to mold or otherwise shape the support member 413032 to have a desired contour, without having the support member 413032 spring back to its neutral position. In any of those embodiments, the housing 412940 can further include an attachment device 413043, such as an adhesive layer attached to the support surface 413033 of the support member 413032 and configured to releaseably attach to the recipient's skin.

An advantage of flexible support members 413032 configured in accordance with embodiments of the invention is that they can be more comfortable for the recipient to receive. A further advantage is that such support members can be less likely to be knocked off the recipient because they can fit closely to the contours of the recipient's skin surface.

Figure 42:
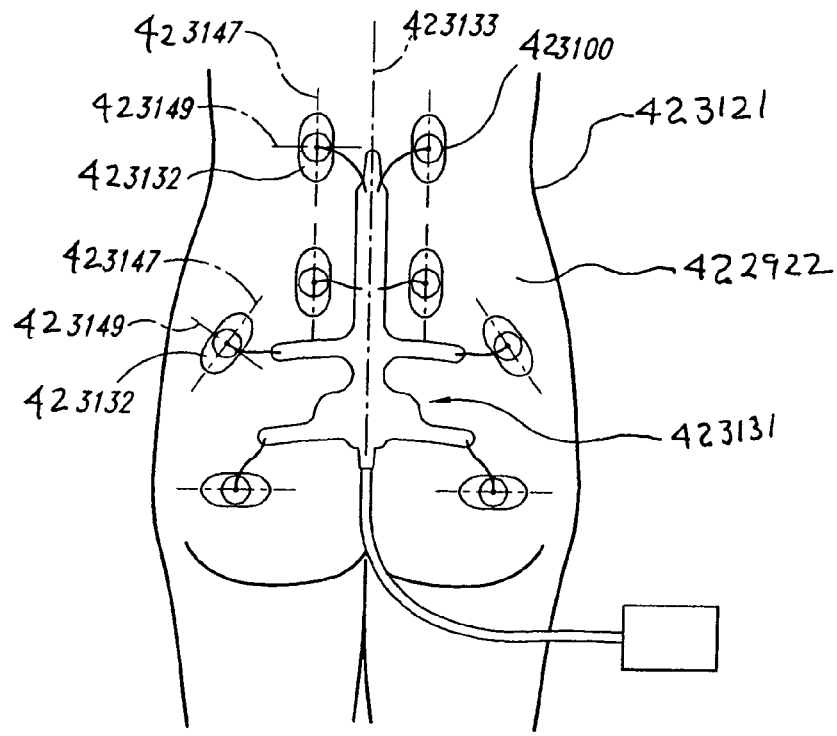
FIGS. 42A-42C illustrate top plan views of percutaneous probe housings having shaped support surfaces configured in accordance with further embodiments of the invention.

FIGS. 42A-42C illustrate top plan views of percutaneous apparatuses 423100 having asymmetric support members in accordance with further embodiments of the invention. In one embodiment, a percutaneous apparatus 423100 (shown in FIG. 42A) includes a housing 423140 having a probe portion 423139 disposed about a probe axis 423145, and a support member 423132 that is asymmetric with respect to the probe axis 423145. In one aspect of the embodiment, the support member 423132 can have a generally elliptical shape, and can accordingly be elongated along a major axis 423147 which is transverse to a minor axis 423149. In other embodiments, the support member 423132 can have other shapes that are also asymmetric relative to the probe axis 423145.

One feature of a housing 423140 having an asymmetric support member 423132 is that it can be placed relatively close to another housing 423140 without overlapping the respective support members, and while still providing a relatively large amount of support member surface area in contact with the recipient's skin surface 422922. For example, as shown in FIG. 42B, two apparatuses 423100 (shown as a first apparatus 423100a and a second apparatus 423100b) can be positioned relatively close to each other by aligning the major axes 423147 of the apparatuses to be at least approximately parallel. The support members 423132 provide a relatively large amount of surface area in contact with the recipient's skin surface 422922, without the support members 423132 overlapping each other. In one aspect of the embodiment, the support members 423132 can be attached to the recipient's skin surface 422922 with an adhesive attachment device generally similar to that described above with reference to FIG. 40A, and in other embodiments, the attachment device can have other arrangements. In still further embodiments, the support members 423132 of the apparatuses 423100 can have a contoured or otherwise non-planar shape, configured in a manner generally similar to that described above with reference to FIGS. 29A-29B.

As shown in FIG. 42C, a plurality of the percutaneous apparatuses 423100 can initially be releasably carried by an apparatus support 423131. The apparatuses 423100 can be deployed from the support 423131 and attached to a recipient 423121 in a variety of orientations. For example, some of the percutaneous apparatuses 423100 can be positioned with their major axes 423147 aligned with the recipient's spine 423133. Other percutaneous apparatuses 423100 can be attached with their major axes 423147 canted at an angle relative to the spine 423133. The relative orientation of the percutaneous apparatuses 423100 can depend on, for example, the proximity of the percutaneous apparatuses 423100 to each other, the proximity of the percutaneous apparatuses to axis 423149 and can be relatively flat relative to the major axis 423147. Accordingly, the support member 423132 can be oriented so that its contour best matches the local contour of the recipient's skin surface 422922.

Figure 43:
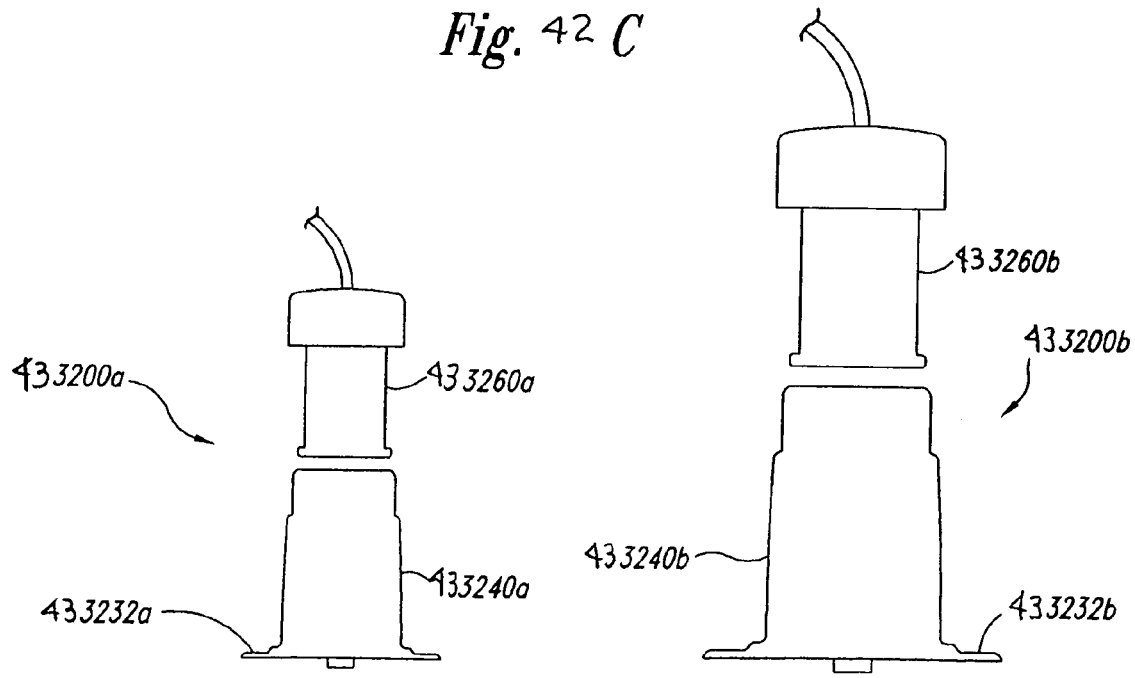
FIG. 43 is a partially schematic, side elevational view of a pair of percutaneous housings having different sizes in accordance with still another embodiment of the invention.

In other embodiments, the percutaneous apparatuses can have other characteristics that make them particularly suitable for specific applications. For example, as shown in FIG. 43, a plurality of percutaneous apparatuses 433200 can include a relatively small first percutaneous apparatus 433200a and a relatively larger second percutaneous apparatus 433200b. The first percutaneous apparatus 433200a can include a housing 433240a, a support member 433232a, and an actuator tool 433260a, each having (for example) any of the arrangements and/or characteristics described above with reference to FIGS. 1A-31C. Because the apparatus 433200a can have a relatively small size, it can be particularly suitable for use with children or small adults, or for applications in which the apparatuses 433200a must be positioned close together. For purposes of comparison, the second apparatus 433200b can include a housing 433240b, a support member 433232b, and an actuator tool 433260b having a larger size suitable for adults. In other embodiments, other attributes of the percutaneous apparatus 433200 (such as the size and/or shape of the support member) can vary from one apparatus to another so that an operator can choose the apparatus most suitable for a particular application.

In still further embodiments, an operator can couple multiple percutaneous apparatuses between a single control unit 10 (FIG. 1E) and a single recipient, with at least two of the percutaneous apparatuses having different shapes and/or sizes. For example, the operator can attach relatively small percutaneous apparatuses (such as the apparatuses 433200a) to a region of the recipient's skin surface at which the percutaneous apparatuses are spaced closely together. The operator can attach relatively large percutaneous apparatuses (such as the apparatuses 433200b) to a region of the recipient's skin surface at which the percutaneous apparatuses are spaced farther apart. In other embodiments, percutaneous apparatuses having different shapes or other configuration aspects can be coupled between a single controller 10 and a single recipient to more closely couple the configurations of the apparatuses with the locations at which they are attached.

Modifications of the above embodiments of the invention will be apparent to those skilled in the art. For example, while aspects of the invention were described in the context of percutaneous electrical therapy in which electrodes are used to deliver electricity to a patient, features of the invention may be used with electrodes designed for medical monitoring and/or diagnosis. In addition, features of this invention may be used with acupuncture needles or other needles not used for conducting electricity to or from a patient, such as liquid delivery and/or extraction needles.

We claim:

1. A percutaneous apparatus, comprising:
   an elongated percutaneous electrode having a first sharp end, and an opposite second end with first and second segments, the first and second segments being configured to resiliently return toward a neutral position, the first and second segments configured to form a bend therebetween so that at least part of the first segment faces toward at least part of the second segment; and
   a coupling member having an aperture, the aperture having an electrically conductive portion, the aperture being sized to removably receive the first and second segment so that the second end contacts the electrically conductive portion.

2. The percutaneous apparatus of claim 1, wherein the aperture has a diameter smaller than the space between the first and second segments.

3. The apparatus of claim 1, wherein the first segment and the second segment are formed from a single conductive member.

4. The apparatus of claim 1, wherein the percutaneous electrode includes a resilient, conductive material with at least one of the first and second segments being movable relative to the other, and wherein the conductive material has a first configuration when the at least part of the first segment is spaced apart from the at least part of the second segment by a first distance, the conductive material further having a second configuration with the at least part of the first segment spaced apart from the at least part of the second segment by a second distance less than the first distance, the conductive material being elastically changeable from the first configuration to the second configuration.

5. The apparatus of claim 1, further comprising:
   a housing with the percutaneous electrode movably received in the housing; and
   an attachment device coupled to the housing and releasably coupleable to a recipient's skin.

6. The apparatus of claim 1, wherein
   the first and second segments and the bend form a button hook shape that is removably receiveable in the aperture of the coupling member.

7. The apparatus of claim 1, wherein
   the second end of the electrode being configures to form multiple bends, and each of said bends having first and second segments facing one another.

8. A percutaneous apparatus, comprising:
   a percutaneous electrode having a first sharp end and an opposite second end with first and second segments, at least part of the first segment being aligned along an axis, at least part of the second end being offset from the axis, the first and second segments being configured to form a bend so that the first and second segments face one another; and
   a coupling member having an aperture, the aperture having an aperture wall with at least a portion of the aperture wall being electrically conductive, the aperture being sized to removably receive the first and second segments, and at least one of the first and second segments being in contact with the electrically conductive portion of the aperture wall.

9. The apparatus of claim 8, wherein the percutaneous electrode includes a resilient, conductive material with at least one of the first and second segments being movable relative to the other, and wherein the conductive material has a first configuration when the at least part of the first segment is spaced apart from the at least part of the second segment by a first distance, the conductive material further having a second configuration with the at least part of the first segment spaced apart from the at least part of the second segment by a second distance less than the first distance, the conductive material being elastically changeable from the first configuration to the second configuration.

10. The apparatus of claim 8, wherein
    the first and second segments and the bend form a button hook shape that is removably receiveable in the aperture of the coupling member.

11. The apparatus of claim 8, wherein
    the second end of the electrode being configures to form multiple bends, and each of said bends having first and second segments facing one another.

12. A percutaneous apparatus, comprising:
    a percutaneous electrode having opposite first and second ends, the second end having first and second segments, the first segment being aligned along a first axis, a part of the second segment being aligned along a second axis offset from the first axis, and the first and second segments being configured to define an approximately 180 degree bend therebetween; and
    a coupling member having an aperture, the aperture having an aperture wall with at least a portion of the aperture wall being electrically conductive, the aperture being sized to removably receive the first and second segments of the percutaneous electrode and the approximately 180 degree bend being in contact with the electrically conductive portion of the aperture wall.

13. The apparatus of claim 12, wherein
    the first and second segments and the bend form a button hook shape that is removably receiveable in the aperture of the coupling member.

14. The apparatus of claim 12, wherein
    the second end of the electrode being configures to form multiple bends, and each of said bends includes first and second segments facing one another.

* * * * *